US009872502B2

(12) United States Patent
Spangenberg et al.

(10) Patent No.: US 9,872,502 B2
(45) Date of Patent: Jan. 23, 2018

(54) BRACHIARIA-UROCHLOA ENDOPHYTES

(75) Inventors: German Carlos Spangenberg, Bundoora (AU); Kathryn Michaela Guthridge, Hadfield (AU)

(73) Assignee: Agriculture Victoria Services Pty Ltd, Attwood (AU)

( * ) Notice: Subject to any disclaimer, the term of this patent is extended or adjusted under 35 U.S.C. 154(b) by 0 days.

(21) Appl. No.: 14/127,786

(22) PCT Filed: Jun. 1, 2012

(86) PCT No.: PCT/AU2012/000620
§ 371 (c)(1),
(2), (4) Date: Dec. 19, 2013

(87) PCT Pub. No.: WO2012/174585
PCT Pub. Date: Dec. 27, 2012

(65) Prior Publication Data
US 2014/0201868 A1 Jul. 17, 2014

(30) Foreign Application Priority Data
Jun. 20, 2011 (AU) .................. 2011902393

(51) Int. Cl.
| *A01N 63/00* | (2006.01) |
|---|---|
| *A01N 65/00* | (2009.01) |
| *A01H 15/00* | (2006.01) |
| *A01N 63/04* | (2006.01) |
| *C07K 14/37* | (2006.01) |
| *C12N 9/02* | (2006.01) |
| *C12P 17/18* | (2006.01) |
| *C12R 1/645* | (2006.01) |
| *A01N 43/90* | (2006.01) |
| *A01N 65/44* | (2009.01) |

(52) U.S. Cl.
CPC ............. *A01N 65/00* (2013.01); *A01H 15/00* (2013.01); *A01N 43/90* (2013.01); *A01N 63/04* (2013.01); *A01N 65/44* (2013.01); *C07K 14/37* (2013.01); *C12N 9/0008* (2013.01); *C12P 17/182* (2013.01); *C12R 1/645* (2013.01); *C12Y 102/01009* (2013.01)

(58) Field of Classification Search
CPC ....... A01N 65/00; A01N 43/90; C12P 17/182; C12N 9/0008
USPC ........................................................ 424/93.5
See application file for complete search history.

(56) References Cited

U.S. PATENT DOCUMENTS

| 5,162,228 A | 11/1992 | Sumino et al. |
|---|---|---|
| 6,072,107 A | 6/2000 | Latch et al. |
| 6,111,170 A | 8/2000 | Latch et al. |
| 2012/0144533 A1* | 6/2012 | Craven .................. 800/300 |

FOREIGN PATENT DOCUMENTS

| AU | 73853/91 | 10/1991 |
|---|---|---|
| WO | 2004106487 A2 | 12/2004 |
| WO | 2008100892 A2 | 8/2008 |

OTHER PUBLICATIONS

Fernandez-Trujillo et al. Isolation of Acremonium Species Causing Postharvest Decay of Peaches in Spain; Plant Disease, vol. 81, No. 8 (1997) pp. 958.1.*
Grunewaldt-Stocker et al. Plant Health Effects of Acremonium Root Endophytes Compared to Those of Arbuscular Mycorrhiza; Roots: the Dynamic Interface between Plants and the Earth (2003) pp. 445-454.*
Hacker, J.B. Sexuality and Hybridization in Signal Grass, *Brachiaria Decumbens*; Tropical Grasslands, vol. 22, No. 3 (1988) pp. 139-144.*
Kelemu et al. The Role of Endophytic Fungi in *Brachiaria*, A Tropical Forage Grass; International Grassland Congress (19, 2001). Proceedings. Brazilian Society of Animal Husbandry, pp. 605-607 downloaded from http://www.international.grasslands.org/files/igc/publications/2001/tema16-2.pdf on Apr. 27, 2015.*
Abello, J. et al. "Agrobacterium-mediated transformation of the endophytic fungus Acremonium implicatum associated with Brachiaria grasses" Mycological Research, 2008, pp. 407-413, vol. 112.
Tanaka, A. et al. "peramine synthetase [Epichloe festucae]" 2012, GenBank:BAE06845, Retrieved from http://www.ncbi.nlm.nih.gov/protein/BAE06845.
Jungmann, L. et al. "Isolation and characterization of microsatellite markers for Brachiaria brizantha (Hochst. ex A. Rich. ) Stap", Conserv Genet. 2009, pp. 1873-1876, vol. 10.
Kelemu, S. et al. "An endophyte of the tropical forage grass Brachiaria brizantha: Isolating, identifying, and characterizing the fungus, and determining its antimycotic properties", Can. Microbiol., 2001, pp. 55-62, vol. 47.
Kimura, H. et al. "Cloning and Sequencing of the Putative Glyceraldehyde-3-Phosphate Dehydrogenase Gene from Cephalosporium acremonium and Its Application to Herterologous Gene Expression", Journal of Fermentation and Bioengineering, 1991, pp. 145-150, vol. 71, No. 3.
White, T. et al. "Amplification and Direct Sequencing of Fungal Ribosomal RNA Genes for Phylogenetics", PCR Protocols, 1990, pp. 315-322, Academic Press, Inc.
International Preliminary Report on Patentability for PCT/AU2012/000620, dated Dec. 23, 2013.
Statement of Grounds and Particulars of Opposition filed on Aug. 10, 2015 against corresponding Australian Patent Application No. 2012272544.

(Continued)

*Primary Examiner* — Scott Long
*Assistant Examiner* — Paul Martin
(74) *Attorney, Agent, or Firm* — Larson & Anderson, LLC

(57) ABSTRACT

The present invention relates to fungi of *Acremonium* spp, wherein said fungi are purified or isolated from plants of the *Brachiaria-Urochloa* complex and wherein, when said fungi are inoculated into a plant, said plant has improved resistance to diseases and/or pests relative to an uninocualated control plant. The present invention also relates to plants inoculated with such fungi, products produced by the fungi and related genes, proteins and methods.

14 Claims, 10 Drawing Sheets

(56) References Cited

OTHER PUBLICATIONS

CRT Seed Buyer's Guide (3 ED), New Endophyte Technologies, Aug. 2006.
Easton, H.S., Grasses and Neotyphodium endophytes: co-adaptation and adaptive breeding, Euphytica, 2007, pp. 295-306, vol. 154.
Tapper, B.A. et al., Selection against toxin production in endophyte-infected perennial ryegrass, Grassland Research and Practice Series No. 7, 1999, pp. 107-111.
Zhikai, G. et al, Initial Identification and Resistance Analysis of Endophytic Fungus Strain HND5 Isolated from *Brachiaria* sp., Chinese Journal of Tropical Crops, 2007, p. 96, vol. 28, No. 2, English Abstract only.

\* cited by examiner

Group 1 Endophytes
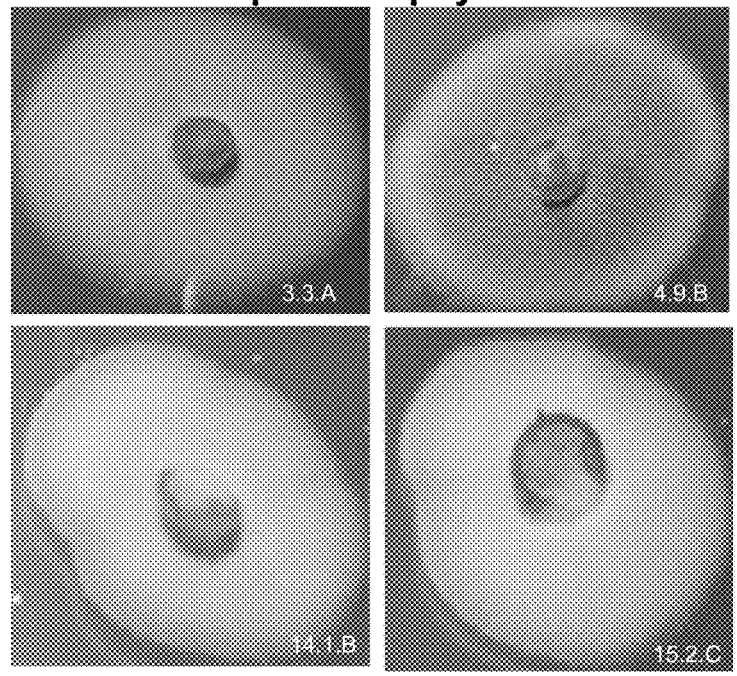
Group 2 Endophytes
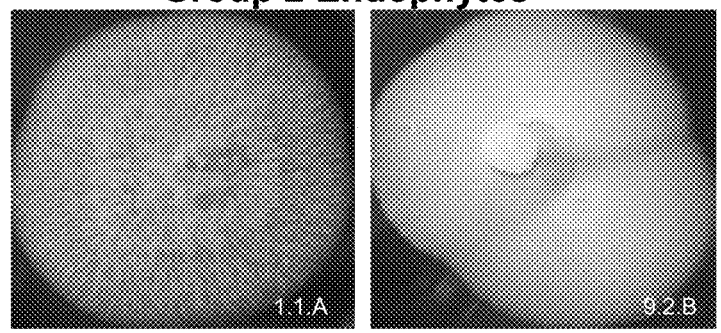
Group 3 Endophyte    Group 4 Endophyte
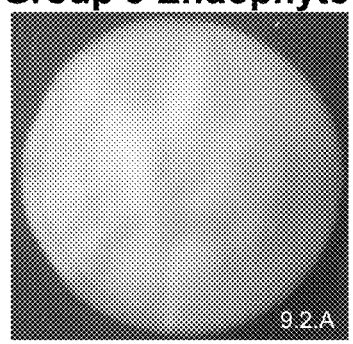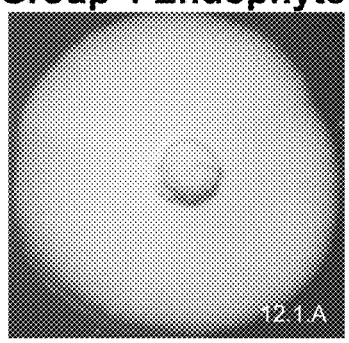
FIGURE 4

```
1_0                             813 gacctcgtcgtcaacggcaagaaggtcaagttctacactgagcgcgaccccgctgccatc 872
BrE_1_1A_v31_n42297064              ............................c..............c......t 97013
BrE_9_2A_n143        104330    .....t.....g...........a..cgt......gg...............c...... 104389
BrE_5_1B _n1085        1887    ................t...................c...a.g..t..g......... 1946
BrE_3_3A _n6036        1081    ................t...................c...a.g..t..g......... 1140
BrE_12_1E_n4653        1200    ................t...................c...a.g..t..g......... 1141

1_0                             873 ccctggtccgagaccggtgccgactacattgtcgagtccactggtgtcttcaccaccacc 932
BrE_1_1A_v31_n42297012         ......aag..c.....c.....g.....c..t.........c.................. 96953
BrE_9_2A_n143        104390    ......aag.....t.cc.....g...g........................t... 104449
BrE_5_1B _n1085        1947    ..g...aag..c.....c.....g.....c.........c.................t 2006
BrE_3_3A _n6036        1141    ..g...aag..c.....c.....g.....c.........c.................t 1200
BrE_12_1E_n4653        1140    ..g...aag..c.....c.....g.....c.........c.................t 1081

1_0                             933 gagaaggcctccgcccacttgaagggtggtgccaagaaggtcatcatctctgccccctct 992
BrE_1_1A_v31_n42296952         ..c.....tg....t.........c.....................c......t..g 96893
BrE_9_2A_n143        104450    ..c......aag.....tc.tc....................tg..........t..t... 104509
BrE_5_1B _n1085        2007    .........ggt..t..................................g......... 2066
BrE_3_3A _n6036        1201    .........ggt..t..................................g......... 1260
BrE_12_1E_n4653        1080    .........ggt..t..................................g......... 1021

1_0                             993 gctgatgccccatgtacgttatgggtgtcaacaacgagacctacgatggctccgccgac 1052
BrE_1_1A_v31_n42296892         ..c................g..............g.ga..........c...aag.....t 96833
BrE_9_2A_n143        104510    ..c...c....................g.ga..........c...aag........ 104569
BrE_5_1B _n1085        2067    ..c...............c......c......g.ga..t.g......c...ag....a.. 2126
BrE_3_3A _n6036        1261    ..c...............c......c......g.ga..t.g......c...ag....a.. 1320
BrE_12_1E_n4653        1020    ..c...............c......c......g.ga..t.g......c...ag....a.. 961

1_0                            1053 gtcatctccaacgcctcttgcaccaccaactgcttggctccctcgccaaggtcatccac 1112
BrE_1_1A_v31_n42296832         ...........t.............c..............................    96773
BrE_9_2A_n143        104570    ........t.....t...........c...................c..... 104629
BrE_5_1B _n1085        2127    ......g..g.......................c..........g........a.. 2186
BrE_3_3A _n6036        1321    ......g..g.......................c..........g........a.. 1380
BrE_12_1E_n4653         960    ......g..g.......................c..........g........a.. 901

1_0                            1113 gacaacttcaccatcgtcgagggtctcatgaccaccgtccactcctacaccgccacccag 1172
BrE_1_1A_v31_n42296772         .....g...gg...t..........................t..........         96713
BrE_9_2A_n143        104630    .....g...ggt.....t...........a.......t............... 104689
BrE_5_1B _n1085        2187    .....g........t.........c..g.........a.....g............... 2246
BrE_3_3A _n6036        1381    .....g........t.........c..g.........a.....g............... 1440
BrE_12_1E_n4653         900    .....g........t.........c..g.........a.....g............... 841
```

FIGURE 10

```
1_0                     1  tcatcgtcgagggcccccgtcctcgctgcgggttacctcaacgatgacgctaagacggcga  60
BrE_12_1E_n4848         1  ............................................................  60
BrE_5_1B_n2956       6640  ............................................................ 6581
BrE_3_3A_n9655

1_0                    61  gggcgtacatcgagaatcccgcctgggtccgtaaggcgcacttccggcccgctcagcccc 120
BrE_12_1E_n4848        61  ............................................................ 120
BrE_5_1B_n2956       6580  .................g..........c............................... 6521
BrE_3_3A_n9655       6623  .................g........................................... 6573

1_0                   121  gccgccggttctaccgcacggggatcttgggcgtcaggctgtcgacggatctattacat 180
BrE_12_1E_n4848       121  ............................................................ 180
BrE_5_1B_n2956       6520  ..........................................................c. 6461
BrE_3_3A_n9655       6572  ..........................................................c..c. 6573

1_0                   181  tcataggccgtgctgatttccaggttaaggttcgtggccagcgtatggagctcggggagg 240
BrE_12_1E_n4848       181  ............................................................ 240
BrE_5_1B_n2956       6460  ....c.....c.......t.......................................... 6401
BrE_3_3A_n9655       6512  ....c.....c...............................t.................. 6453

1_0                   241  tgcggtcgcatattgtggcttgcctgcctgaggctgttgacattcacgtcgacgtcatct 300
BrE_12_1E_n4848       241  ............................................................ 300
BrE_5_1B_n2956       6400  ....a.................................t..c................... 6341
BrE_3_3A_n9655       6452  ......................................t..c................... 6393

1_0                   301  gtcccgagggggagaaggtcctcgcggccttcctctcgttcggcaagggtggcgatgatg 360
BrE_12_1E_n4848       301  ............................................................ 360
BrE_5_1B_n2956       6340  .........................a.........g...............c.......... 6281
BrE_3_3A_n9655       6392  .........................a.........g...............c.......... 6333

1_0                   361  gccagcagcagaagcagcagcagcagcagcagcagggcgctatccgagtccaccagcccg 420
BrE_12_1E_n4848       361  ............................................................ 420
BrE_5_1B_n2956       6280  .........................a.......---......................... 6224
BrE_3_3A_n9655       6332  .........................a.......---......................... 6276

1_0                   421  accaggctctggcggattcgctccgctccatggtcgaaaagctgagacagactctgccac 480
BrE_12_1E_n4848       421  ............................................................ 480
BrE_5_1B_n2956       6223  ..........a.............................g.................... 6164
BrE_3_3A_n9655       6275  ..........a.............................g.................... 6216

1_0                   481  ctgctgcggttccatcgttcttcgttcccataaccgggtttccctacctcgtctcgggga 540
BrE_12_1E_n4848       481  ............................................................ 540
BrE_5_1B_n2956       6163  ..............................g..................g.......... 6104
BrE_3_3A_n9655       6215  ..............................g...g..............g.......... 6156

1_0                   541  aggtagatcggcggagcctgttgagcttcgccaacgggtcgtcggtggaggagctggcgt 600
BrE_12_1E_n4848       541  ............................................................ 600
BrE_5_1B_n2956       6103  ...............................t..............c............. 6044
BrE_3_3A_n9655       6155  ...............................t..............c............. 6096
```

FIGURE 12

SEQUENCE LISTING

<160> NUMBER OF SEQ ID NOS: 10

<210> SEQ ID NO 1
<211> LENGTH: 360
<212> TYPE: DNA
<213> ORGANISM: Neurospora crassa

<400> SEQUENCE: 1

| | | | | | | |
|---|---|---|---|---|---|---|
| gacctcgtcg | tcaacggcaa | gaaggtcaag | ttctacactg | agcgcgaccc | cgctgccatc | 60 |
| ccctggtccg | agaccggtgc | cgactacatt | gtcgagtcca | ctggtgtctt | caccaccacc | 120 |
| gagaaggcct | ccgcccactt | gaagggtggt | gccaagaagg | tcatcatctc | tgcccctct | 180 |
| gctgatgccc | ccatgtacgt | tatgggtgtc | aacaacgaga | cctacgatgg | ctccgccgac | 240 |
| gtcatctcca | acgcctcttg | caccaccaac | tgcttggctc | cctcgccaa | ggtcatccac | 300 |
| gacaacttca | ccatcgtcga | gggtctcatg | accaccgtcc | actcctacac | cgccacccag | 360 |

<210> SEQ ID NO 2
<211> LENGTH: 352
<212> TYPE: DNA
<213> ORGANISM: Acremonium

<400> SEQUENCE: 2

| | | | | | | |
|---|---|---|---|---|---|---|
| cgtcaacggc | aagaaggtca | agttctacac | cgagcgcgac | cccgccgcca | ttccctggaa | 60 |
| ggacaccggc | gccgagtaca | tcgttgagtc | caccggtgtc | ttcaccacca | ccgacaaggc | 120 |
| tgccgctcac | ttgaagggcg | gtgccaagaa | ggtcatcatc | tccgcccctt | cggccgatgc | 180 |
| ccccatgtac | gtgatgggtg | tcaacgagaa | gacctacgac | ggcaaggccg | atgtcatctc | 240 |
| caacgcttct | tgcaccacca | actgcctggc | tcccctcgcc | aaggtcatcc | acgacaagtt | 300 |
| cggcattgtc | gagggtctca | tgaccaccgt | ccactcctac | actgccaccc | ag | 352 |

<210> SEQ ID NO 3
<211> LENGTH: 360
<212> TYPE: DNA
<213> ORGANISM: Acremonium

<400> SEQUENCE: 3

| | | | | | | |
|---|---|---|---|---|---|---|
| gaccttgtcg | tgaacggcaa | gaagatccgt | ttctacggtg | agcgcgaccc | cgccgccatc | 60 |
| ccctggaagg | agactgccgc | cgagtacgtt | gtcgagtcca | ctggtgtctt | caccactacc | 120 |
| gacaaggcca | aggcccatct | tcagggtggt | gccaagaagg | ttgtcatctc | tgctccttct | 180 |
| gccgacgccc | ccatgtacgt | tatgggtgtc | aacgagaaga | cctacgacgg | caaggccgat | 240 |
| gtcatctcta | acgcttcttg | caccaccaac | tgcctggctc | cctcgccaa | ggtcctccac | 300 |
| gacaagttcg | gtatcgttga | gggtctcatg | accaccatcc | actcttacac | cgccacccag | 360 |

<210> SEQ ID NO 4
<211> LENGTH: 360
<212> TYPE: DNA
<213> ORGANISM: Acremonium

<400> SEQUENCE: 4

| | | | | | | |
|---|---|---|---|---|---|---|
| gacctcgtcg | tcaatggcaa | gaaggtcaag | ttctacaccg | agagggatcc | ggctgccatc | 60 |
| ccgtggaagg | acaccggcgc | cgagtacatc | gtcgagtcca | ccggtgtctt | caccaccact | 120 |
| gagaaggccg | gtgctcactt | gaagggtggt | gccaagaagg | tcatcatctc | ggcccctct | 180 |
| gccgatgccc | ccatgtacgt | catgggcgtc | aacgagaagt | cgtacgacgg | cagcgccaac | 240 |

```
gtcatctcca acgcgtcgtg caccaccaac tgcctggctc ccctggccaa ggtcatcaac    300
gacaagttca ccattgtcga gggcctgatg accaccatcc acgcctacac cgccacccag    360
```

<210> SEQ ID NO 5
<211> LENGTH: 360
<212> TYPE: DNA
<213> ORGANISM: Acremonium

<400> SEQUENCE: 5

```
gacctcgtcg tcaatggcaa gaaggtcaag ttctacaccg agagggatcc ggctgccatc     60
ccgtggaagg acaccggcgc cgagtacatc gtcgagtcca ccggtgtctt caccaccact    120
gagaaggccg gtgctcactt gaagggtggt gccaagaagg tcatcatctc ggcccctct    180 gccgatgccc ccatgtacgt catgggcgtc aacgagaagt cgtacgacgg cagcgccaac    240
gtcatctcca acgcgtcgtg caccaccaac tgcctggctc ccctggccaa ggtcatcaac    300
gacaagttca ccattgtcga gggcctgatg accaccatcc acgcctacac cgccacccag    360
```

<210> SEQ ID NO 6
<211> LENGTH: 360
<212> TYPE: DNA
<213> ORGANISM: Acremonium

<400> SEQUENCE: 6

```
gacctcgtcg tcaatggcaa gaaggtcaag ttctacaccg agagggatcc ggctgccatc     60
ccgtggaagg acaccggcgc cgagtacatc gtcgagtcca ccggtgtctt caccaccact    120
gagaaggccg gtgctcactt gaagggtggt gccaagaagg tcatcatctc ggcccctct    180 gccgatgccc ccatgtacgt catgggcgtc aacgagaagt cgtacgacgg cagcgccaac    240
gtcatctcca acgcgtcgtg caccaccaac tgcctggctc ccctggccaa ggtcatcaac    300
gacaagttca ccattgtcga gggcctgatg accaccatcc acgcctacac cgccacccag    360
```

<210> SEQ ID NO 7
<211> LENGTH: 600
<212> TYPE: DNA
<213> ORGANISM: Epichloe festucae

<400> SEQUENCE: 7

```
tcatcgtcga gggccccgtc ctcgctgcgg gttacctcaa cgatgacgct aagacggcga     60
gggcgtacat cgagaatccc gcctgggtcc gtaaggcgca cttccggccc gctcagcccc    120
gccgccggtt ctaccgcacg ggggatcttg ggcgtcaggc tgtcgacgga tctattacat    180
tcataggccg tgctgatttc caggttaagg ttcgtggcca gcgtatggag ctcggggagg    240
tgcggtcgca tattgtggct tgcctgcctg aggctgttga cattcacgtc gacgtcatct    300
gtcccgaggg ggagaaggtc ctcgcggcct tcctctcgtt cggcaagggt ggcgatgatg    360
gccagcagca gaagcagcag cagcagcagc agcaggcgc tatccgagtc caccagcccg    420
accaggctct ggcggattcg ctccgctcca tggtcgaaaa gctgagacag actctgccac    480
ctgctgcggt tccatcgttc ttcgttccca taacccgggtt tccctacctc gtctcgggga    540
aggtagatcg gcggagcctg ttgagcttcg ccaacgggtc gtcggtggag gagctggcgt    600
```

<210> SEQ ID NO 8
<211> LENGTH: 600
<212> TYPE: DNA
<213> ORGANISM: Acremonium

<400> SEQUENCE: 8

```
tcatcgtcga gggccccgtc ctcgctgcgg gttacctcaa cgatgacgct aagacggcga    60
gggcgtacat cgagaatccc gcctgggtcc gtaaggcgca cttccggccc gctcagcccc   120
gccgccggtt ctaccgcacg ggggatcttg ggcgtcaggc tgtcgacgga tctattacat   180
tcataggccg tgctgatttc caggttaagg ttcgtggcca gcgtatggag ctcggggagg   240
tgcggtcgca tattgtggct tgcctgcctg aggctgttga cattcacgtc gacgtcatct   300
gtcccgaggg ggagaaggtc ctcgcggcct tcctctcgtt cggcaagggt ggcgatgatg   360
gccagcagca gaagcagcag cagcagcagc agcagggcgc tatccgagtc caccagcccg   420
accaggctct ggcggattcg ctccgctcca tggtcgaaaa gctgagacag actctgccac   480
ctgctgcggt tccatcgttc ttcgttccca taaccgggtt tccctacctc gtctcgggga   540
aggtagatcg gcggagcctg ttgagcttcg ccaacgggtc gtcggtggag gagctggcgt   600
```

<210> SEQ ID NO 9
<211> LENGTH: 597
<212> TYPE: DNA
<213> ORGANISM: Acremonium

<400> SEQUENCE: 9

```
tcatcgtcga gggccccgtc ctcgctgcgg gttacctcaa cgatgacgct aagacggcga    60
gggcgtacat cgagaatccc gcgtgggtcc gcaaggcgca cttccggccc gctcagcccc   120
gccgccggtt ctaccgcacg ggggatcttg ggcgtcaggc tgtcgacgga tctattacct   180
tcatcggccg cgctgatttt caggttaagg ttcgtggcca gcgtatggag ctcggggagg   240
tgcgatcgca tattgtggct tgcctgcctg aggctgttga tatccacgtc gacgtcatct   300
gtcccgaggg ggagaaggtc ctcgcggcct tcctatcgtt cggcgagggt ggcgatgacg   360
gccagcagca gaagcagcag cagcaacagc agggcgctat ccgagtccac cagcccgacc   420
aggctctagc ggattcgctc cgctccatgg tcgagaagct gagacagact ctgccacctg   480
ctgcggttcc atcgttcttc gttcccgtaa ccgggtttcc ctacctggtc tcggggaagg   540
tagatcggcg gagcctgttg agcttcgcca atgggtcgtc ggtggagcag ctggcgt      597
```

<210> SEQ ID NO 10
<211> LENGTH: 528
<212> TYPE: DNA
<213> ORGANISM: Acremonium

<400> SEQUENCE: 10

```
tcgagaatcc cgcgtgggtc cgtaaggcgc acttccggcc cgctcagccc cgccgccggt    60
tctaccgcac ggggatcttg ggcgtcagg ctgtcgacgg atctatcacc ttcatcggcc   120
gcgctgattt ccaggttaag gttcgtggtc agcgtatgga gctcggggag gtgcggtcgc   180
atattgtggc ttgcctgcct gaggctgttg atatccacgt cgacgtcatc tgtcccgagg   240
gggagaaggt cctcgcggcc ttcctatcgt tcggcgaggg tggcgatgac ggccagcagc   300
agaagcagca gcagcaacag cagggcgcta tccgagtcca ccagcccgac caggctctag   360
cggattcgct ccgctccatg gtcgagaagc tgagacagac tctgccacct gctgcggttc   420
catcgttctt cgttcccgta ccgggtttc cctacctggt ctcggggaag gtagatcggc   480
ggagcctgtt gagcttcgcc aatgggtcgt cggtggagca gctggcgt               528
```

BRACHIARIA-UROCHLOA ENDOPHYTES

FIELD OF THE INVENTION

The present invention relates to fungi, plants infected with fungi, products produced by fungi, and related methods.

BACKGROUND OF THE INVENTION

Microbes represent an invaluable source of novel genes and compounds that have the potential to be utilised in a range of industrial sectors. Scientific literature gives numerous accounts of microbes being the primary source of antibiotics, immunosuppressants, anticancer agents and cholesterol-lowering drugs, in addition to their use in environmental decontamination and in the production of food and cosmetics. A relatively unexplored group of microbes known as endophytes, which reside in the tissues of living plants, offer a particularly diverse source of novel compounds and genes that may provide important benefits to society, and in particular, agriculture.

Endophytes often form mutualistic relationships with their hosts, with the endophyte conferring increased fitness to the host, often through the production of defence compounds. At the same time, the host plant offers the benefits of a protected environment and nutriment to the endophyte.

Members of the *Brachiaria-Urochloa* species complex belong to the Poaceae family of grasses. Some species of *Brachiaria-Urochloa* are economically significant tropical forage grasses that have been released as commercial cultivars and include *B. brizantha, B. decumbens, B. dictyoneura, B. humidicola*, and *B. ruziziensis*, as well as corresponding interspecific and intraspecific hybrids.

Genetic diversity analysis based on internal transcribed spacer (ITS) nuclear ribosomal DNA sequence data indicates a strong affinity between *Urochloa* and *Brachiaria*, supporting morphological and anatomical studies that show a continuous gradation between these grass genera.

Seed-transmitted endophytic fungi have been observed in *B. brizantha*. These endophytes may play a role in protecting *Brachiaria-Urochloa* from fungal pathogens, such as *Drechslera* spp., which cause leaf spots.

There is a general lack of information and knowledge of the fungal endophytes of the *Brachiaria-Urochloa* species complex as well as of methods for the identification and characterization of novel endophytes and their deployment in *Brachiaria-Urochloa* plant improvement programs.

It is an objection of the present application to overcome, or at least alleviate, one or more of the difficulties or deficiencies associates with the prior art.

SUMMARY OF THE INVENTION

This invention describes methods for the identification, isolation, characterisation and inoculation of novel endophytes from and in *Brachiaria-Urochloa*, respectively, that may be used to establish novel endophyte-*Brachiaria/Urochloa* associations for improved pasture production for livestock industries.

The discovery, characterization, and inoculation of novel fungal endophytes in associations with *Brachiaria-Urochloa* pasture grasses may assist in the varietal development process of these pasture grasses for livestock production in warmer climates around the world.

Many of the commercially developed *Brachiaria-Urochloa* pasture grasses are aposporous apomicts. These grasses reproduce asexually through seed without a requirement for gamete union, hence propagating the maternal genotype.

Apomictic reproduction has a number of key advantages for research on, and use of, fungal endophyte-grass host associations. The practical implication of seed transmission of endophytes in *Brachiaria-Urochloa* is significant; once associated with the plant, the fungus can perpetuate itself through seed, provided that seed storage conditions do not reduce the survival of the fungus.

In a first aspect, the present invention provides a substantially purified or isolated fungus of *Acremonium* spp, wherein said fungus is purified or isolated from a plant of the *Brachiaria-Urochloa* species complex and wherein, when said fungus is inoculated into a plant, said plant has improved resistance to diseases and/or pests relative to an uninocualated control plant.

Preferably, the fungus is selected from the group consisting of *Acremonium* 1.1.A, *Acremonium* 3.3.A, *Acremonium* 3.3.B, *Acremonium* 3.3.C, *Acremonium* 4.9.A, *Acremonium* 4.9.B, *Acremonium* 5.1.A, *Acremonium* 5.1.B, *Acremonium* 5.1.D, *Acremonium* 5.1.E, *Acremonium* 7.1.A, *Acremonium* 8.1.A, *Acremonium* 8.1.B, *Acremonium* 8.1.C, *Acremonium* 9.2.A, *Acremonium* 9.2.B, *Acremonium* 9.2.C, *Acremonium* 10.1.A, *Acremonium* 11.1.A, *Acremonium* 12.1.A, *Acremonium* 12.1.B, *Acremonium* 12.1.C, *Acremonium* 12.1.D *Acremonium* 12.1.E, *Acremonium* 14.1.B, *Acremonium* 14.1.C, *Acremonium* 15.2.C, *Acremonium* 15.2.D, *Acremonium* 15.2.E, as described herein.

Representative samples, namely *Acremonium* 1.1.A (1.1A), 3.3.A (3.3A), 5.1.B (5.1B), 9.2.A (9.2A) and 12.1.A (12.1A) were deposited at The National Measurement Institute. 1/153 Bertie Street, Port Melbourne, Victoria, Australia, 3207, on 7 Jun. 2011 with accession numbers V11/011370, V11/011371, V11/011372, V11/011373, and V11/011374, respectively. Replacement deposits were made on Apr. 15, 2016 in response to a notification of non-viability, and were assigned the same accession numbers.

By 'substantially purified' is meant that the fungus is free of other organisms. The term therefore includes, for example, a fungus in axenic culture. Preferably, the fungus is at least approximately 90% pure, more preferably at least approximately 95% pure, even more preferably at least approximately 98% pure, even more preferably at least approximately 99% pure.

The term 'isolated' means that the fungus is removed from its original environment (eg. the natural environment if it is naturally occurring). For example, a naturally occurring fungus present in a living plant is not isolated, but the same fungus separated from some or all of the coexisting materials in the natural system, is isolated.

In its natural environment, the fungus may be an endophyte, i.e. live mutualistically within a plant. Alternatively, the fungus may be an epiphyte, i.e. grow attached to or upon a plant. Preferably, the fungus is a fungal endophyte.

The fungus of the present invention may, in its natural environment, be associated with a plant of the *Brachiaria-Urochloa* species complex. More particularly, the plant of the *Brachiaria-Urochloa* species complex is selected from the group consisting of *Brachiaria brizantha, Brachiaria decumbens, Brachiaria humidicola, Brachiaria stolonifera, Brachiaria ruziziensis, Urochloa brizantha, Urochloa decumbens, Urochloa humidicola, Urochloa mosambicensis, Brachiaria marlothii, Brachiaria nigropedata, Urochloa dictyoneura, Urochloa oligotricha, Urochloa panicoides, Brachiaria obtusiflora, Brachiaria serrifolia, Urochloa advena, Urochloa arrecta, Urochloa brachyura, Urochloa*

*eminii, Urochloa mollis, Urochloa xantholeuca, Urochloa oligotricha, Urochloa panicoides, Urochloa plantaginea, Urochloa platynota* and *Urochloa xantholeuca*, as well as interspecific and intraspecific hybrids of *Brachiaria-Urochloa* species complex.

In a particularly preferred embodiment, the plant of the *Brachiaria-Urochloa* complex is selected from the group consisting of *Brachiaria brizantha, Brachiaria decumbens, Brachiaria humidicola* and *Urochloa mosambicensis.*

By 'associated with' in this context is meant that the fungus lives on, in or in close proximity to the plant. For example, it may be endophytic, for example living within the internal tissues of the plant, or epiphytic, for example growing externally on the plant.

The fungus may be a heterotroph that uses organic carbon for growth, more particularly a saprotroph that obtains nutrients by consuming detritus.

In a further aspect, the present invention provides a plant inoculated with a fungus as hereinbefore described, said plant comprising a fungus-free host plant stably infected with said fungus. Preferably, the plant with which the fungus is associated has improved resistance to pests and/or diseases relative to an uninoculated control plant. In a preferred embodiment, the improved resistance to pests and/or diseases includes insecticidal or insect repellent activity. In a further preferred embodiment, the improved resistance to pests and/or diseases includes antifungal activity.

In a preferred embodiment, the host plant may be inoculated with more than one fungal strain according to the present invention.

Preferably, the plant is an agricultural plant such as a grass species, preferably forage, turf or bioenergy grasses, such as those belonging to the *Brachiaria-Urochloa* species complex (panic grasses) including *Brachiaria brizantha, Brachiaria decumbens, Brachiaria humidicola, Brachiaria stolonifera, Brachiaria ruziziensis, B. dictyoneura, Urochloa brizantha, Urochloa decumbens, Urochloa humidicola, Urochloa mosambicensis* as well as interspecific and intraspecific hybrids of *Brachiaria-Urochloa* species complex, and those belonging to the genera *Lolium* and *Festuca*, including *L. perenne* (perennial ryegrass) and *L. arundinaceum* (tall fescue) and *L. multiflorum* (Italian ryegrass).

Preferably, the plant is infected with the fungus by a method selected from the group consisting of inoculation, breeding, crossing, hybridization and combinations thereof.

The fungus-infected plants may be cultured by known techniques. The person skilled in the art can readily determine appropriate culture conditions depending on the plant to be cultured.

In a further aspect, the present invention provides a plant, plant seed or other plant part derived from a plant of the present invention and stably infected with a fungus of the present invention. Preferably, the plant, plant seed or other plant part with which the fungus is associated has improved resistance to pests and/or diseases relative to an uninoculated control plant, plant seed or other plant part. In a preferred embodiment, the improved resistance to pests and/or diseases includes insecticidal or insect repellent activity. In a further preferred embodiment, the improved resistance to pests and/or diseases includes antifungal activity.

Preferably, the plant cell, plant, plant seed or other plant part is from a grass, more preferably a forage, turf or bioenergy grass, such as those belonging to the *Brachiaria-Urochloa* species complex (panic grasses), including *Brachiaria brizantha, Brachiaria decumbens, Brachiaria humidicola, Brachiaria stolonifera, Brachiaria ruziziensis, B. dictyoneura, Urochloa brizantha, Urochloa decumbens, Urochloa humidicola, Urochloa mosambicensis* as well as interspecific and intraspecific hybrids of *Brachiaria-Urochloa* species complex such as interspecific hybrids between *Brachiaria ruziziensis*×*Brachiaria brizantha, Brachiaria ruziziensis*×*Brachiaria decumbens*, [*Brachiaria ruziziensis*×*Brachiaria decumbens*]×*Brachiaria brizantha*, [*Brachiaria ruziziensis*×*Brachiaria brizantha*]×*Brachiaria decumbens* and those belonging to the genera *Lolium* and *Festuca*, including *L. perenne* (perennial ryegrass) and *L. arundinaceum* (tall fescue) and *L. multiflorum* (Italian ryegrass).

By 'plant cell' is meant any self-propagating cell bounded by a semi-permeable membrane and containing plastid. Such a cell also required a cell wall if further propagation is desired. Plant cell, as used herein includes, without limitation, seeds suspension cultures, embryos, meristematic regions, callus tissue, leaves, roots, shoots, gametophytes, sporophytes, pollen and microspores.

In a further aspect, the present invention provides use of a fungus as hereinbefore described to produce a plant stably infected with said fungus. Preferably, the plant with which the fungus is associated has improved resistance to pests and/or diseases relative to an uninoculated control plant. In a preferred embodiment, the improved resistance to pests and/or diseases includes insecticidal or insect repellent activity. In a further preferred embodiment, the improved resistance to pests and/or diseases includes antifungal activity.

In a further aspect of the present invention, there is provided a method of increasing resistance to pests and/or diseases in a plant, said method including inoculating said plant with a fungus as hereinbefore described. Preferably, the plant with which the fungus is associated has improved resistance to pests and/or diseases relative to an uninoculated control plant. In a preferred embodiment, the improved resistance to pests and/or diseases includes insecticidal or insect repellent activity. In a further preferred embodiment, the improved resistance to pests and/or diseases includes antifungal activity.

In a further aspect of the present invention, the fungus may be selected and/or characterised by a method including:
providing a plurality of samples of fungi;
subjecting said fungi to genetic analysis;
subjecting said fungi to metabolic analysis; and
selecting fungi having a desired genetic and metabolic profile.

In a preferred embodiment, this aspect of the invention may include the further step of assessing geographic origin of the fungi and selecting fungi having a desired genetic and metabolic profile and a desired geographic origin.

In a preferred embodiment, the plurality of samples of fungi may be provided by a method including:
providing a plurality of plant samples that may contain fungi; and
isolating fungi from said plant samples.

In a preferred embodiment, the genetic analysis includes detecting the presence or absence of polymorphic markers such as simple sequence repeats.

Applicant has found that specific detection of fungi in planta with markers such as SSR markers has provided the tools for efficient assessment of fungus genetic diversity in diverse grass populations and the potential discovery of novel fungal strains.

By a 'plurality' of samples of endophytes or plant samples is meant a number sufficient to enable a comparison of genetic and metabolic profiles of individual fungal endophytes. Preferably, between approximately 10 and 1,000,000 samples of endophytes or plant samples are provided, more preferably between approximately 100 and 1,000 samples of endophytes or plant samples.

By 'genetic analysis' is meant analysing the nuclear and/or mitochondrial DNA of the endophyte.

This analysis may involve detecting the presence or absence of polymorphic markers, such as simple sequence repeats (SSRs) or mating-type markers. SSRs, also called microsatellites, are based on a 1-7 nucleotide core element, more typically a 1-4 nucleotide core element, that is tandemly repeated. The SSR array is embedded in complex flanking DNA sequences. Microsatellites are thought to arise due to the property of replication slippage, in which the DNA polymerase enzyme pauses and briefly slips in terms of its template, so that short adjacent sequences are repeated. Some sequence motifs are more slip-prone than others, giving rise to variations in the relative numbers of SSR loci based on different motif types. Once duplicated, the SSR array may further expand (or contract) due to further slippage and/or unequal sister chromatid exchange. The total number of SSR sites is high, such that in principle such loci are capable of providing tags for any linked gene.

SSRs are highly polymorphic due to variation in repeat number and are co-dominantly inherited. Their detection is based on the polymerase chain reaction (PCR), requiring only small amounts of DNA and suitable for automation. They are ubiquitous in eukaryotic genomes and have been found to occur in fungal genomes and in plant genomes. Consequently, SSRs are ideal markers for a broad range of applications such as genetic diversity analysis, genome mapping, trait mapping and marker-assisted selection.

Alternatively, or in addition, the genetic analysis may involve sequencing genomic and/or mitochondrial DNA and performing sequence comparisons to assess genetic variation between fungi. In a preferred embodiment, the internal transcribed spacer (ITS) sequence may be used for genetic analysis.

By 'metabolic analysis' is meant analysing metabolites, in particular toxins, produced by the fungi. Preferably, this is done by preparation of inoculated plants for each of the fungi and measurement of toxin levels in planta. More preferably, this is done by preparation of isogenically inoculated plants for each of the fungi and measurement of toxin levels in planta.

By a 'desired genetic and metabolic profile' is meant that the fungus includes genetic and metabolic characteristics that result in a beneficial phenotype in a plant harbouring, or otherwise associated with, the fungus.

Such beneficial properties include improved tolerance to water and/or nutrient stress and improved resistance to pests and/or diseases in the plant with which the fungus is associated. In a preferred embodiment, the beneficial properties include insecticidal or insect repellent activity. In a further preferred embodiment, the improved resistance to pests and/or diseases includes antifungal activity.

For example, resistance to pests and/or diseases in the plant may be increased by at least approximately 5%, more preferably at least approximately 10%, more preferably at least approximately 25%, more preferably at least approximately 50%, more preferably at least approximately 100%, relative to an uninoculated plant that does not contain the fungal endophyte. Preferably, resistance to pests and/or diseases in the plant may be increased by between approximately 5% and approximately 50%, more preferably between approximately 10% and approximately 25%, relative to an uninoculated plant that does not contain the fungal endophyte.

In a further aspect, the present invention provides a method of culturing a fungus as hereinbefore described, said method including growing said fungus on a medium including a source of carbohydrates, for example a starch/sugar-based agar or broth such as potato dextrose agar or potato dextrose broth, or a cereal-based agar or broth such as oatmeal agar or oatmeal broth.

The fungus may be cultured under aerobic or anaerobic conditions.

In a particularly preferred embodiment, the fungus may be cultured in a culture medium including potato dextrose or oatmeal, for example potato dextrose agar, oatmeal agar, potato dextrose broth or oatmeal broth.

The fungus may be cultured for a period of approximately 1 to approximately 100 days, more preferably from approximately 10 to approximately 50 days more preferably from approximately 10 to approximately 30 days.

In a preferred embodiment, the fungus may be cultured in a bioreactor. By a 'bioreactor' is meant a device or system that supports a biologically active environment, such as a vessel in which is carried out a chemical process involving fungi of the present invention and/or products thereof. The chemical process may be aerobic or anaerobic. The bioreactor may have a volume ranging in size from milliliters to cubic meters, for example from approximately 50 ml to approximately 50,000 liters. The bioreactor may be operated via batch culture, batch feed culture, perfusion culture or continuous culture, for example continuous culture in a stirred-tank bioreactor. Fungi cultured in the bioreactor may be suspended or immobilized.

In a preferred embodiment, the method may include the further step of recovering an organic compound produced by the fungus from within fungal cells, including intracellular tissues, from the culture medium (e.g. secreted liquids) or from the air space (e.g. secreted vapours) associated with the culture medium or fungus.

Vapours may arise directly from the fungus or from the secreted liquids which transition between vapour and liquid phases.

The step of recovering the organic compound is preferably done by separating cells from the culture medium or capturing vapours associated with the culture medium or fungus.

Preferably the organic compound is then isolated or purified by a method selected from the group consisting of gas chromatography, liquid chromatography, fractional distillation and absorption chromatography, such as pressure swing adsorption.

By an 'organic compound' is meant a chemical compound whose molecules contain carbon.

In a preferred embodiment, the organic compound may have insecticidal or insect repellent activity. In a particularly preferred embodiment, the organic compound may be peramine or an analogue, derivative or salt thereof.

By a 'derivative' is meant an organic compound obtained from, or regarded as derived from, a compound of the present invention. Examples of derivatives include compounds where the degree of saturation of one or more bonds has been changed (e.g., a single bond has been changed to a double or triple bond) or wherein one or more atoms are replaced with a different atom or functional group. Examples of different atoms and functional groups may include, but are not limited to hydrogen, halogen, oxygen, nitrogen, sulphur, hydroxy, alkoxy, alkyl, alkenyl, alkynyl, amine, amide, ketone and aldehyde.

Preferably, said organic compound is produced by a method as hereinbefore described.

In a preferred embodiment, the organic compound may be obtained from a fungus of the present invention.

In a still further aspect of the present invention, there is provided use of an organic compound according to the present invention as an insecticide or insect repellant.

In a still further aspect of the present invention, there is provided use of an organic compound according to the present invention as an antifungal compound.

In a further aspect of the present invention, there is provided a method of producing an organic compound, said method including culturing a fungus as hereinbefore described under conditions suitable to produce said organic compound. Preferably the conditions are as hereinbefore described.

Preferably the organic compound is peramine or an analogue, derivative or salt thereof.

In a preferred embodiment, the method may include the further step of recovering an organic compound produced by the fungus as hereinbefore described.

On the basis of the deposits referred to above, the entire genome of a fungus of *Acremonium* spp., selected from the group consisting *Acremonium* 1.1.A (1.1A), 3.3.A (3.3A), 5.1.B (5.1B), 9.2.A (9.2A) and 12.1.A (12.1A) is incorporated herein by reference.

Thus, in a further aspect, the present invention includes identifying and/or cloning nucleic acids including genes encoding polypeptides that are involved in the production of organic compounds of the present invention, for example genes encoding enzymes from one or more biochemical pathways which result in the synthesis of said organic compounds.

By a 'biochemical pathway' is meant a plurality of chemical reactions occurring within a cell which are catalysed by more than one enzyme or enzyme subunit and result in the conversion of a substrate into a product. This includes, for example, a situation in which two or more enzyme subunits (each being a discrete protein coded by a separate gene) combine to form a processing unit that converts a substrate into a product. A 'biochemical pathway' is not constrained by temporal or spatial sequentially.

Methods for identifying and/or cloning nucleic acids encoding such genes are known to those skilled in the art and include creating nucleic acid libraries, such as cDNA or genomic libraries, and screening such libraries, for example using probes, for genes encoding enzymes from synthetic pathways for said organic compounds; or mutating the genome of the fungus of the present invention, for example using chemical or transposon mutagenesis, identifying changes in the production of an organic compound of the present invention, and thus identifying genes encoding enzymes from synthetic pathways for said organic compound.

Thus, in a further aspect of the present invention, there is provided a substantially purified or isolated nucleic acid encoding a polypeptide involved in the production of an organic compound of the present invention.

In a preferred embodiment, the nucleic acid may encode a polypeptide involved in the production of peramine or an analogue, derivative or salt thereof.

In a preferred embodiment, the nucleic acid may include a gene encoding glyceraldehyde 3-phosphate dehydrogenase (GAPDH), or a functionally active fragment or variant thereof. In a particularly preferred embodiment, the nucleic acid may include a nucleotide sequence selected from the group consisting of sequences shown in Sequence ID Nos. 2, 3, 4, 5 and 6 hereto and functionally active fragments and variants thereof.

In a preferred embodiment, the nucleic acid may include a perA gene, or a functionally active fragment or variant thereof. In a particularly preferred embodiment, the nucleic acid may include a nucleotide sequence selected from the group consisting of sequences shown in Sequence ID Nos. 8, 9 and 10 hereto and functionally active fragments and variants thereof.

By 'nucleic acid' is meant a chain of nucleotides capable of carrying genetic information. The term generally refers to genes or functionally active fragments or variants thereof and/or other sequences in the genome of the organism that influence its phenotype. The term 'nucleic acid' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

By a 'nucleic acid encoding a polypeptide involved in the production of an organic compound of the present invention' is meant a nucleic acid encoding an enzyme normally present in a fungus of the present invention, which catalyses a step in the pathway that results in synthesis of the organic compound of the present invention.

The present invention encompasses functionally active fragments and variants of the nucleic acids of the present invention. By 'functionally active' in relation to the nucleic acid is meant that the fragment or variant (such as an analogue, derivative or mutant) is capable of manipulating synthesis of an organic compound of the present invention, for example by being translated into an enzyme that is able to participate in the pathway that results in synthesis of the organic compound. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes.

Preferably the fragment has a size of at least 20 nucleotides, more preferably at least 50 nucleotides, more preferably at least 100 nucleotides, more preferably at least 200 nucleotides, more preferably at least 500 nucleotides.

By 'conservative nucleic acid changes' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:
Nonpolar: Ala, Val, Leu, Ile, Pro, Met, Phe, Trp
Uncharged polar: Gly, Ser, Thr, Cys, Tyr, Asn, Gln
Acidic: Asp, Glu
Basic: Lys, Arg, His
Other conservative amino acid substitutions may also be made as follows:
Aromatic: Phe, Tyr, His
Proton Donor: Asn, Gln, Lys, Arg, His, Trp
Proton Acceptor: Glu, Asp, Thr, Ser, Tyr, Asn, Gln In a further aspect of the present invention, there is provided a genetic construct including a nucleic acid according to the present invention.

By 'genetic construct' is meant a recombinant nucleic acid molecule.

In a preferred embodiment, the genetic construct according to the present invention may be a vector.

By a 'vector' is meant a genetic construct used to transfer genetic material to a target cell.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the target cell.

In a preferred embodiment of this aspect of the invention, the genetic construct may further include a promoter and a terminator; said promoter, gene and terminator being operatively linked.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'→5' direction along the nucleic acid.

The promoter and terminator may be of any suitable type and may be endogenous to the target cell or may be exogenous, provided that they are functional in the target cell.

A variety of terminators which may be employed in the genetic constructs of the present invention are also well known to those skilled in the art. The terminator may be from the same gene as the promoter sequence or a different gene. Particularly suitable terminators are polyadenylation signals.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns, antibiotic resistance genes and other selectable marker genes [such as the neomycin phosphotransferase (nptII) gene, the hygromycin phosphotransferase (hph) gene], and reporter genes (such as beta-glucuronidase (GUS) gene (gusA)]. The genetic construct may also contain a ribosome binding site for translation initiation. The genetic construct may also include appropriate sequences for amplifying expression.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

Preferably, the genetic construct is substantially purified or isolated. By 'substantially purified' is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (e.g. a cDNA or a genomic or cDNA fragment produced by PCR or restriction endonuclease digestion) independent of other sequences. It also includes a genetic construct which is part of a hybrid gene encoding additional polypeptide sequence. Preferably, the substantially purified genetic construct is at least approximately 90% pure, more preferably at least approximately 95% pure, even more preferably at least approximately 98% pure, even more preferably at least approximately 99% pure.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), northern and western blot hybridisation analyses.

The genetic constructs of the present invention may be introduced into plants or fungi by any suitable technique. Techniques for incorporating the genetic constructs of the present invention into plant cells or fungal cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant or fungus to be transformed, and may be readily determined by an appropriately skilled person. For transformation of plant protoplasts, PEG-mediated transformation is particularly preferred. For transformation of fungal protoplasts, electroporation and PEG-mediated transformation are particularly preferred. For transformation of fungal hyphae, *Agrobacterium*-mediated transformation is particularly preferred.

Cells incorporating the genetic constructs of the present invention may be selected, as described below, and then cultured in an appropriate medium to regenerate transformed plants or fungi, using techniques well known in the art. The culture conditions, such as temperature, pH and the like, will be apparent to the person skilled in the art. The resulting plants may be reproduced, either sexually or asexually, using methods well known in the art, to produce successive generations of transformed plants or fungi.

The present invention also provides a substantially purified or isolated polypeptide involved in the production of an organic compound of the present invention.

In a preferred embodiment, the polypeptide may be involved in the production of peramine or an analogue, derivative or salt thereof.

In a preferred embodiment, the polypeptide may be encoded by a nucleic acid according to the present invention.

The present invention encompasses functionally active fragments and variants of the polypeptides of the present invention. By 'functionally active' in this context is meant that the fragment or variant has one or more of the biological properties of the corresponding protein from which the fragment or variant is derived. Additions, deletions, substitutions and derivatizations of one or more of the amino acids are contemplated so long as the modifications do not result in loss of functional activity of the fragment or variant. Preferably the fragment or variant has at least approximately 80% identity to the relevant part of the above mentioned sequence to which the fragment or variant corresponds, more preferably at least approximately 90% identity, more preferably at least approximately 95% identity, most preferably at least approximately 98% identity. Such functionally active variants and fragments include, for example, those having conservative amino acid substitutions of one or more residues in the corresponding amino acid sequence.

Preferably the fragment has a size of at least 10 amino acids, more preferably at least 20 amino acids, more preferably at least 50 amino acids, more preferably at least 100 amino acids, more preferably at least 200 amino acids. As used herein, except where the context requires otherwise, the term "comprise" and variations of the term, such as "comprising", "comprises" and "comprised", are not intended to exclude further additives, components, integers or steps.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

DETAILED DESCRIPTION OF THE EMBODIMENTS

The present invention will now be more fully described with reference to the accompanying examples and drawings. It should be understood, however, that the description following is illustrative only and should not be taken in any way as a restriction on the generality of the invention described above.

DESCRIPTION OF THE FIGURES

FIG. 4. Morphology of representative fungal endophytes isolated from *Brachiaria-Urochloa* grass species. Endophyte isolates are grouped based on ITS sequence analysis.

FIG. 10. DNA sequence alignment of the GAPDH gene from *Neurospora crassa* with homologues of 5 fungal *Acremonium* endophyte isolates. The 3 different nuclear rDNA ITS groups to which the 5 *Acremonium* isolates belong are as follows: $2^{nd}$ line—Group 2; $3^{rd}$ line—Group 3; Lines 4, 5 and 6—Group 1.

FIG. 12. Alignment of the *Epichloe festucae* perA gene (1_0) with homologous genes from *Acremonium* isolates from ITS group 1 (3.3.A, 5.1.B and 12.1.E).

EXAMPLE 1—MOLECULAR CHARACTERISATION OF BRACHIARIA-UROCHLOA GRASSES

*Brachiaria-Urochloa* grass species seed batches were sourced from within Australia (Table 1). This resource provided the basis for endophyte discovery and characterisation from the grass species complex *Brachiaria-Urochloa*.

TABLE 1

*Brachiaria-Urochloa* species used for endophyte discovery.

| Seed Batch | *Brachiaria* name | *Urochloa* name |
|---|---|---|
| 5 | Brachiaria brizantha (Hochst. ex A. Rich.) Stapf. | Urochloa brizantha (Hochst. ex A. Rich.) R. D. Webster |
| 1, 6, 7, 10, 13, 14 | Brachiaria decumbens Stapf. | Urochloa decumbens (Stapf) R. D. Webster |
| 2, 4, 8, 9, 15 | Brachiaria humidicola (Rendle) Schweick | Urochloa humidicola (Rendle) Morrone & Zuloaga |
| 3, 11, 12 | Brachiaria stolonifera Goos | Urochloa mosambicensis (Hack.) Dandy |

Figure 1:
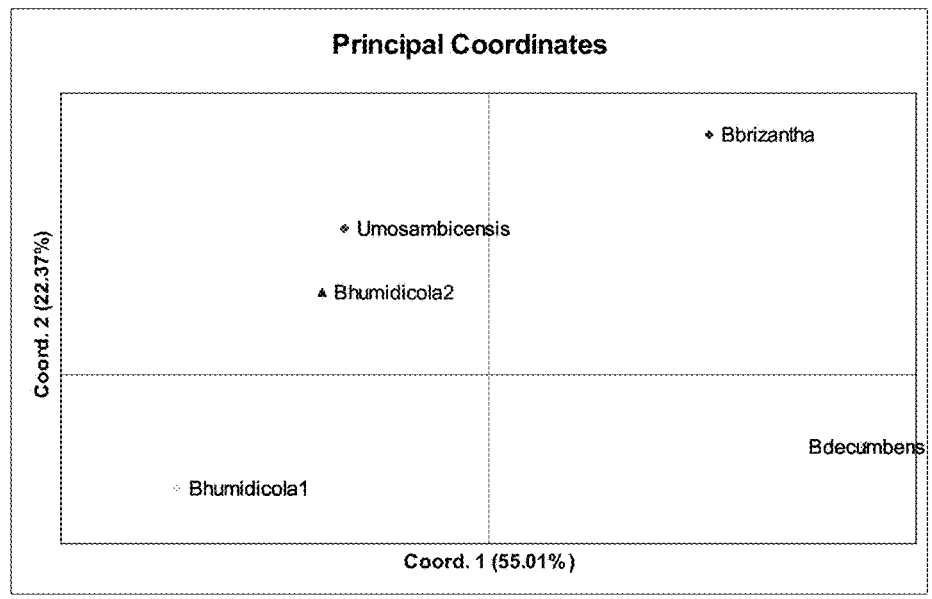
FIG. 1. Principal components analysis (PCA) analysis of genetic diversity between *Brachiaria-Urochloa* grass species using dominantly scored SSR markers.

To characterise the diversity of the grass species and confirm their assignment to the *Brachiaria-Urochloa* complex, genetic diversity analysis was conducted using simple sequence repeat (SSR) markers derived from *Brachiaria-Urochloa*. The primer pairs BbUNICAMP001, BbUNICAMP002, BbUNICAMP003, BbUNICAMP004, BbUNICAMP005, BbUNICAMP006 and BbUNICAMP007 were selected (Jungmann et al. 1999) and used to amplify across species of *Brachiaria-Urochloa*. As the ploidy levels between different *Brachiaria-Urochloa* species varies, alleles for each SSR locus were scored dominantly (presence/absence) and principal components analysis (PCA) was performed (FIG. 1).

Each of the *Brachiaria-Urochloa* species was effectively discriminated using these markers. No variation within populations was observed, as expected for apomictic species. *B. brizantha* and *B. decumbens* are more similar to each other than they are to *B. humidicola* and *U. mosambicensis*. There are two *B. humidicola* populations, with *Humidicola*1 being distinct from *Humidicola*2 and *U. mosambicensis*. The genetically distinct nature of the *Humidicola*1 and *Humidicola*2 plants suggests that there are two different (sub)-species present in the *B. humidicola* seed batches analysed.

EXAMPLE 2—ISOLATION OF FUNGAL ENDOPHYTES FROM *BRACHIARIA-UROCHLOA* GRASSES

Figure 2:
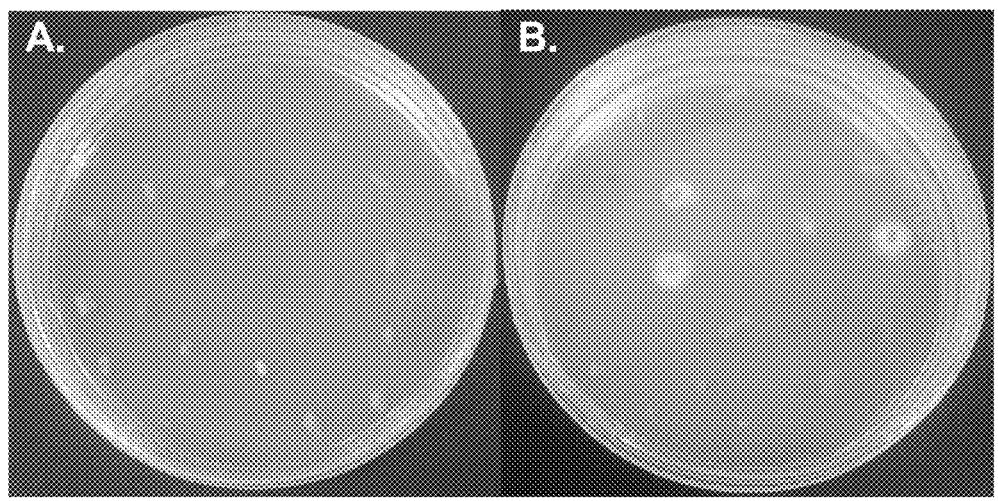
FIG. 2. Isolation of fungal endophytes from *Brachiaria-Urochloa* grass species. A. Surface-sterilised inner tiller explants from *Brachiaria-Urochloa* grass species are placed on potato dextrose agar (PDA) medium and cultured at 25° C. in the dark for fungal endophyte out-growth; B. After 4 weeks, fungal endophytes grow out of the tiller explants and are subcultured onto fresh PDA medium.

Fungal endophytes from *Brachiaria-Urochloa* grasses were isolated from surface-sterilised young tiller explants (FIG. 2). A total of 31 fungal endophytes were isolated and subcultured. Twenty nine fungal endophyte isolates were identified as *Acremonium* species by morphological examination in in vitro culture. Two fungal endophyte isolates (14.1.A and 14.1.D) were not of the *Acremonium* morphotype and were excluded from further analysis. Table 2 shows a summary of the fungal endophytes isolated from *Brachiaria-Urochloa* grasses.

TABLE 2

Summary of purified and subcultured fungal endophytes isolated from *Brachiaria-Urochloa* grasses. Isolate names are coded such that the first number represents the seed batch and the second number the plant number from 20 seed germinated from each seed batch.

| Endophyte isolate ID | Host Plant | Identification based on morphological characteristics |
|---|---|---|
| 1.1.A | B. decumbens | Acremonium sp. |
| 3.3.A | U. mosambicensis | Acremonium sp. |

TABLE 2-continued

Summary of purified and subcultured fungal endophytes isolated from *Brachiaria-Urochloa* grasses. Isolate names are coded such that the first number represents the seed batch and the second number the plant number from 20 seed germinated from each seed batch.

| Endophyte isolate ID | Host Plant | Identification based on morphological characteristics |
|---|---|---|
| 3.3.B | U. mosambicensis | Acremonium sp. |
| 3.3.C | U. mosambicensis | Acremonium sp. |
| 4.9.A | B. humidicola (2) | Acremonium sp. |
| 4.9.B | B. humidicola (2) | Acremonium sp. |
| 5.1.A | B. brizantha | Acremonium sp. |
| 5.1.B | B. brizantha | Acremonium sp. |
| 5.1.D | B. brizantha | Acremonium sp. |
| 5.1.E | B. brizantha | Acremonium sp. |
| 7.1.A | B. decumbens | Acremonium sp. |
| 8.1.A | B. humidicola (1) | Acremonium sp. |
| 8.1.B | B. humidicola (1) | Acremonium sp. |
| 8.1.C | B. humidicola (1) | Acremonium sp. |
| 9.2.A | B. humidicola (1) | Acremonium sp. |
| 9.2.B | B. humidicola (1) | Acremonium sp. |
| 9.2.C | B. humidicola (1) | Acremonium sp. |
| 10.1.A | B. decumbens | Acremonium sp. |
| 11.1.A | U. mosambicensis | Acremonium sp. |
| 12.1.A | U. mosambicensis | Acremonium sp. |
| 12.1.B | U. mosambicensis | Acremonium sp. |
| 12.1.C | U. mosambicensis | Acremonium sp. |
| 12.1.D | U. mosambicensis | Acremonium sp. |
| 12.1.E | U. mosambicensis | Acremonium sp. |
| 14.1.A | B. decumbens | Unknown (Sterile) |
| 14.1.C | B. decumbens | Acremonium sp. |
| 14.1.D | B. decumbens | Possibly Paecilomyces |
| 14.1.B | B. decumbens | Acremonium sp. |
| 15.2.C | B. humidicola (1) | Acremonium sp. |
| 15.2.E | B. humidicola (1) | Acremonium sp. |
| 15.2.D | B. humidicola (1) | Acremonium sp. |

EXAMPLE 3—GENETIC CHARACTERIZATION OF FUNGAL ENDOPHYTES FROM *BRACHIARIA-UROCHLOA* GRASSES

As *Acremonium* is an anamorphic genus, the internal transcribed spacer ITS sequence was used for further characterisation. The entire region of nuclear ribosomal DNA which comprises both internal transcribed spacers ITS1 and ITS2 and the 5.8S subunit was PCR-amplified using primers ITS5 and ITS4 (White et al. 1990). Purified PCR amplification products were sequenced using Sanger sequencing technology. Isolated subcultured endophytes were then grouped based on ITS sequence identity. Sequence data was used in BLASTn analysis to identify matches in the NCBI database (Table 3).

Figure 3:
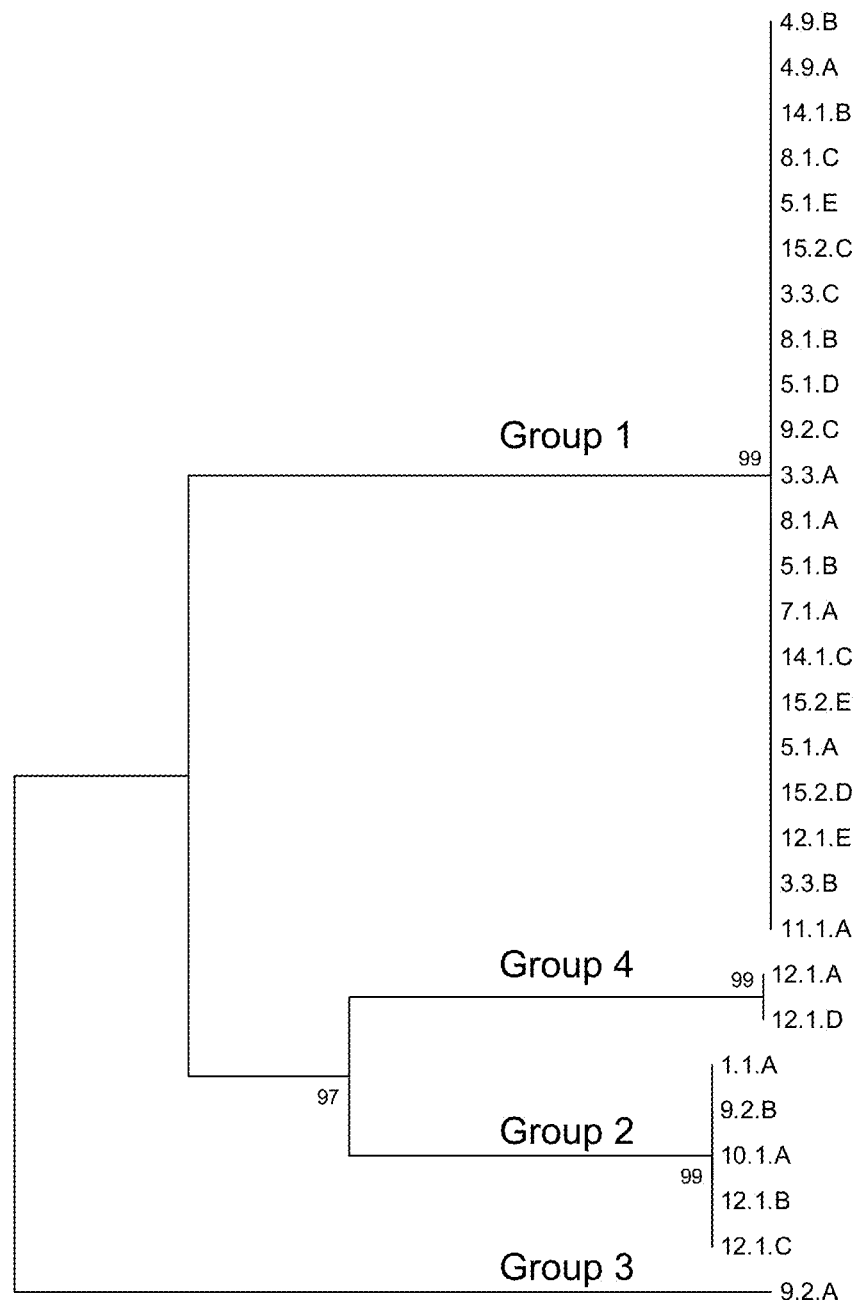
FIG. 3. Neighbour-joining tree obtained from sequence analysis of the nuclear rDNA ITS region for 29 fungal endophytes isolated from *Brachiaria-Urochloa* grass species. After alignment of all ITS sequences, the total contig length was 619 bp and contained 120 parsimony informative sites. The robustness of nodes in the tree was tested by 1000 bootstrap re-samplings. Numbers at branches are bootstrap percentages.

Phylogenetic analysis of 29 fungal endophytes isolated from *Brachiaria-Urochloa* grasses identified 4 distinct clades based on nuclear rDNA ITS sequence (FIG. 3). Morphological differences in the endophytes exist both between and within these ITS groups (FIG. 4). Endophyte isolates within each clade matched (≤99% identity) to a wide range of different Ascomycetes (Table 3). None of the endophyte isolates isolated from the *Brachiaria-Urochloa* grasses displayed 100% identity to the nuclear rDNA ITS sequence from other fungi within the public database, indicating unique fungal endophytes have been isolated.

Molecular analysis of the 29 endophyte isolates with nuclear rDNA ITS data identified presence of multiple endophyte strains within the same plant for plants 9.2 and 12.1 (Table 4). The presence of multiple endophyte strains within the one host plant is not usually observed in other grass species such as perennial ryegrass and tall fescue, suggesting a novel discovery in *Brachiaria*.

TABLE 3

Summary of fungal endophytes isolated from *Brachiaria-Urochloa* grasses characterised using ITS sequence-based analysis. Fungal endophytes are grouped by ITS sequence identity and the closest BLAST match for each ITS clade is shown.

| Group | Accession # | Species - best BLASTn match |
|---|---|---|
| 1 | AB540569 | *Acremonium atrogriseum* |
| 21 *Brachiaria* endophytes | DQ317343 | *Ascomycete* sp. |
| | FJ235936 | Fungal sp. |
| | AB190399 | *Phialophora intermedia* |
| | FM177651 | Uncultured compost fungus |
| 2 | U57674 | *Acremonium alternatum* |
| 1.1.A, 9.2.B, 10.1.A, | FN706550 | *Acremonium egyptiacum* |
| 12.2.B, 12.1.C | HQ649793 | *Acremonium* sp. |
| | EU520092 | *Acremonium strictum* |
| | EU427036 | *Cladosterigma* sp. |
| | EU520121 | *Cytospora chrysosperma* |
| | AM176743 | *Hypocreales* sp. |
| | EU754963 | Uncultured fungus |
| 3 | EF577237 | *Acremonium* sp. |
| 9.2.A | AJ292395 | *Cephalosporium lanosoniveum* |
| | HQ270477 | *Simplicillium lanosoniveum* |
| | FJ861375 | *Simplicillium lanosoniveum* |
| | HQ191403 | Uncultured Dikarya |
| | EF685278 | Uncultured fungus |
| | DQ443734 | *Verticillium fungicola* |
| 4 | AB540572 | *Acremonium dichromosporum* |
| 12.1.A, 12.1.D | AY882946 | *Acremonium exuviarum* |
| | HQ914927 | *Acremonium* sp. |
| | AY632658 | *Emericellopsis donezkii* |
| | AY632657 | *Emericellopsis glabra* |
| | AY632659 | *Emericellopsis humicola* |
| | AB425984 | *Emericellopsis microspora* |
| | AY632660 | *Emericellopsis minima* |
| | AY632667 | *Emericellopsis pallida* |
| | AY632666 | *Emericellopsis salmosynnemata* |
| | HQ914819 | *Emericellopsis* sp. |
| | AY632665 | *Emericellopsis synnematicola* |
| | AB425993 | *Emericellopsis terricola* |
| | AY632671 | *Stanjemonium grisellum* |
| | AY632672 | *Stanjemonium ochroroseum* |
| | FJ939394 | *Stilbella fimetaria* |

TABLE 4

Summary of the number of endophytes isolated from each *Brachiaria* or *Urochloa* plant and the corresponding number of nuclear rDNA ITS groups identified.

| Plant number | Species host | # Endophytes isolated | # ITS groups |
|---|---|---|---|
| 1.1 | *B. decumbens* | 1 | 1 |
| 3.3 | *U. mosambicensis* | 3 | 1 |
| 4.9 | *B. humidicola* 2 | 2 | 1 |
| 5.1 | *B. brizantha* | 4 | 1 |
| 7.1 | *B. decumbens* | 1 | 1 |
| 8.1 | *B. humidicola* 1 | 3 | 1 |
| 9.2 | *B. humidicola* 1 | 3 | 3 |
| 10.1 | *B. decumbens* | 1 | 1 |
| 11.1 | *U. mosambicensis* | 1 | 1 |
| 12.1 | *U. mosambicensis* | 5 | 3 |
| 14.1 | *B. decumbens* | 2 | 1 |
| 15.2 | *B. humidicola* 1 | 3 | 1 |

EXAMPLE 4—INOCULATION OF FUNGAL ENDOPHYTES INTO *BRACHIARIA-UROCHLOA* HOST PLANTS

Figure 5:
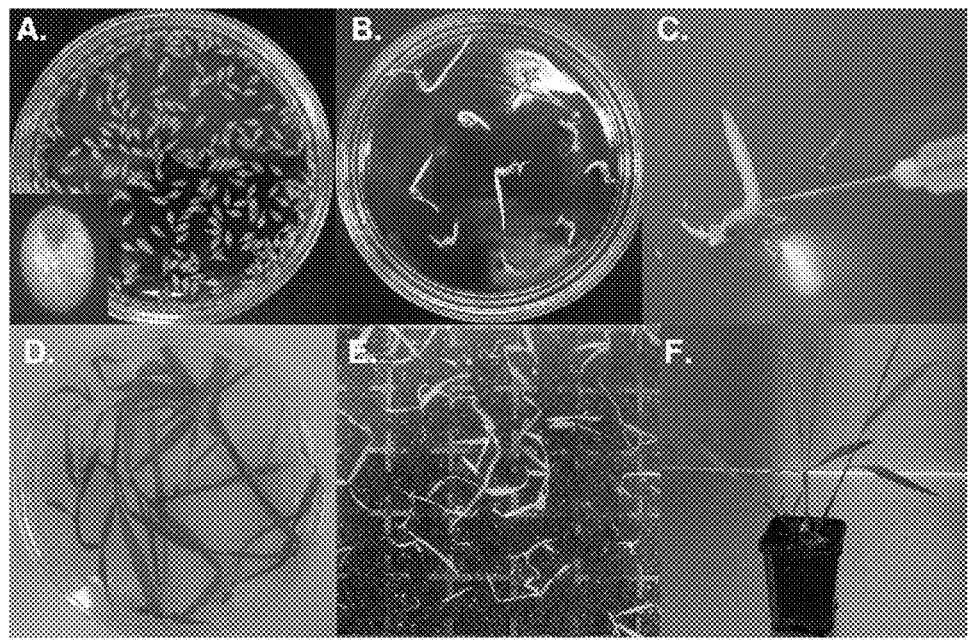
FIG. 5. Seed-derived young seedling inoculation of *Brachiaria-Urochloa* grasses with fungal endophyte mycelium. A. Seeds are scarified (inset) and sterilised; B. Seed germination following 9 days at 26° C. in the dark; C. Young seedlings are inoculated with endophyte mycelium; D. After 4 weeks on MS medium, plantlets are transferred to soil; E. Plantlets growing after 7 days in soil; F. Plants established in soil under glasshouse conditions are tested for endophyte presence and identity using a DNA marker-based assay.
Figure 6:
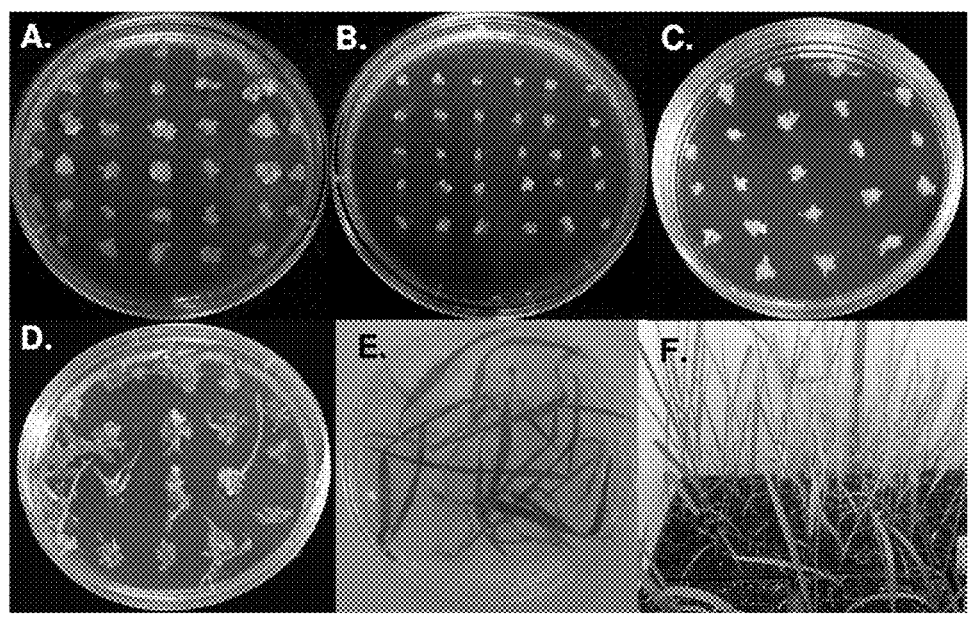
FIG. 6. Inoculation of in vitro regenerating calli from *Brachiaria-Urochloa* grasses with isolated subcultured fungal endophytes. A. Generation of meristem-derived proliferating embryogenic calli of *Brachiaria-Urochloa* grasses; B. Explants from in vitro cultured embryogenic calli of *Brachiaria-Urochloa* grasses; C. Shoot (and root) regeneration followed by endophyte inoculation; D. Plantlet regeneration; E. After 4 weeks on MS medium, plantlets are transferred to soil; F. Mature plants are tested for endophyte presence and identity using a DNA marker-based assay.

Methodologies for inoculating isolated and subcultured fungal endophytes into seedlings (FIG. 5) and regenerating calli (FIG. 6) from *Brachiaria-Urochloa* grass species were developed to enable the generation of novel grass host-fungal endophyte associations between *Brachiaria-Urochloa* grass species and endophytes isolated from a range of pasture grass species (including species within the *Brachiaria-Urochloa* complex).

EXAMPLE 5—METABOLIC PROFILING OF *BRACHIARIA-UROCHLOA* GRASS-ENDOPHYTE ASSOCIATIONS

Mature plants of *Brachiaria-Urochloa* grass-endophyte associations that had been maintained in a controlled environment were subjected to metabolic profiling analysis. Three individual plants (biological replicates) from each seed batch were analysed using liquid chromatography-mass spectrometry (LC-MS), with two technical replicates per plant. Additional plants representing the *Humidicola*1 and *Humidicola*2 sub-groups identified in the SSR-based genetic diversity analysis were selected from seed batches 2, 4 and 8. Freeze-dried pseudostem samples were prepared for LC-MS analysis using an 80% methanol extraction procedure.

Figure 7:
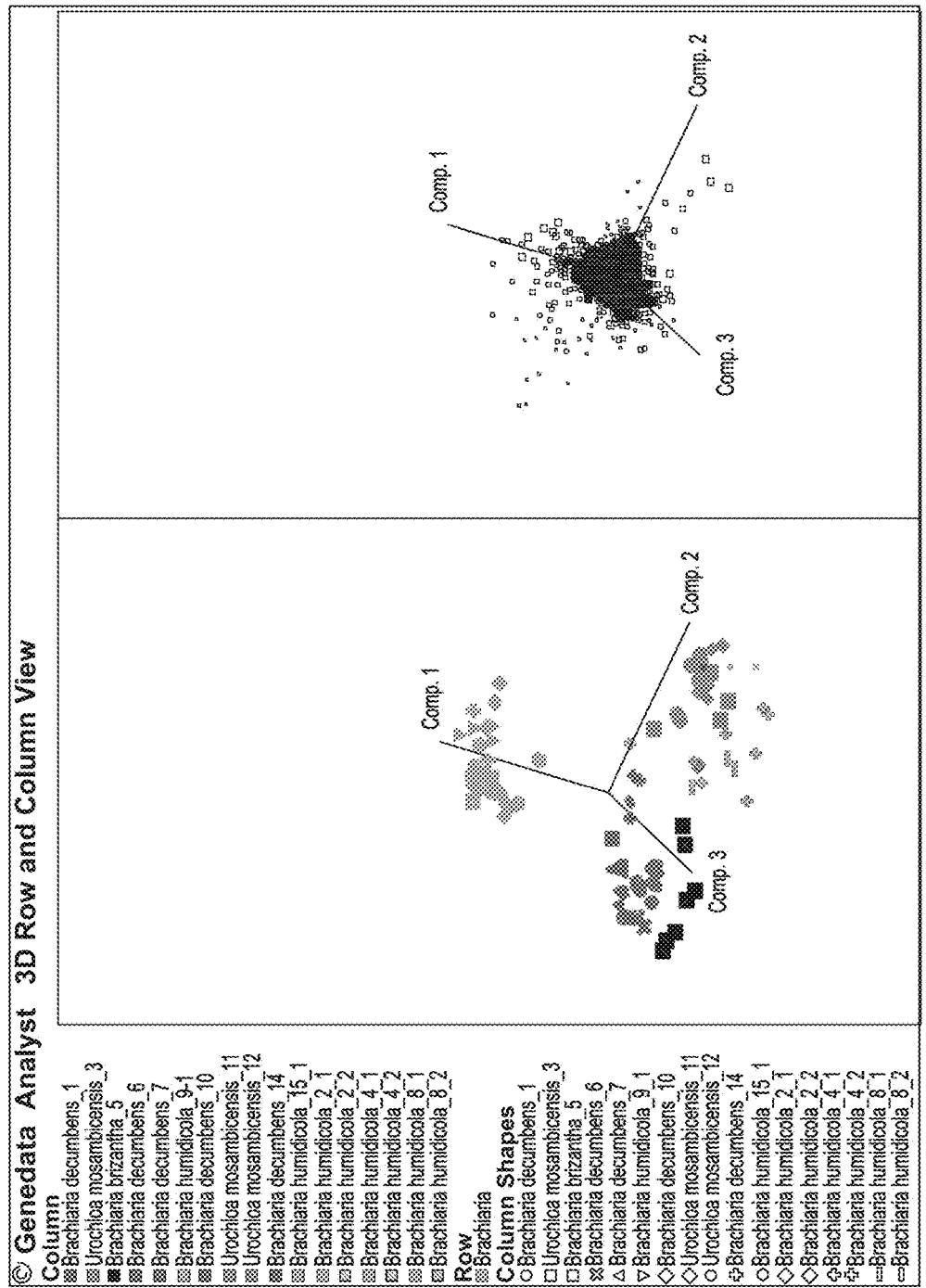
FIG. 7. Principal components analysis (PCA) plot of all metabolite compounds following LC-MS (ITMS+p ESI Full ms [80.00-2000.00]) analysis of pseudostem tissue samples of *B. brizantha, B. decumbens, B. humidicola* and *U. mosambicensis* associated with corresponding fungal endophytes. Technical replicates are shown clustered together. Components 1, 2 and 3 explain up to 19.2% 11.3% and 5.6% of the variability, respectively.

Principal Components Analysis (PCA) based on the full LC-MS dataset reveals differences in metabolic profiles of each *Brachiaria-Urochloa* grass-endophyte association analysed (FIG. 7). Each of the associations forms a distinct cluster, indicating that there is limited variation within a species/population. As for the SSR-based genetic analysis, there are two separate *B. humidicola* populations, with *Humidicola*1 samples forming a separate cluster to the remaining populations. The 3D PCA plot indicates that *B. decumbens* and *B. brizantha* associations share similar metabolic profiles as do *Humidicola*2 and *U. mosambicensis* associations.

Figure 8:
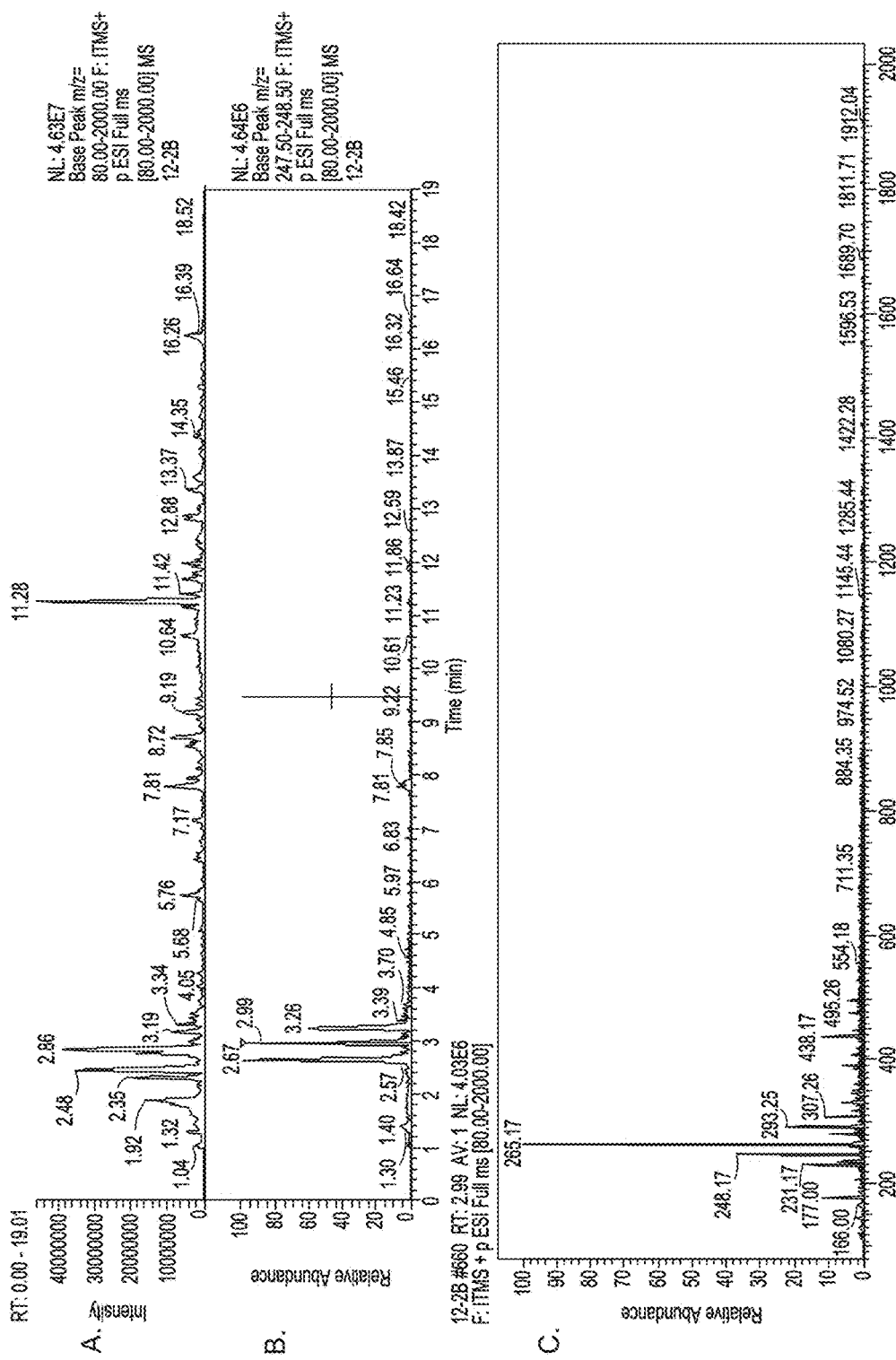
FIG. 8. LC-MS analysis of *Urocholoa mosambicensis* grass-fungal endophyte associations displaying extracted ion chromatogram. A. Positive ion extraction; B. Peramine extracted ion chromatogram m/z 248; C. Mass spectrometry at retention time 3.00 min.

The fungal endophyte-derived compound peramine, known to have insecticidal activity, was produced in planta and was thus identified in the metabolic profiles of the *Urocholoa mosambicensis* grass-fungal endophyte associations (FIG. 3). The presence of peramine was confirmed through MS (ions extracted at the mass-to-charge ratio [m/z] of 248). All samples of the *Urocholoa mosambicensis* grass-fungal endophyte associations tested produced the endophyte-derived insecticidal compound peramine (Table 5 and FIG. 8).

TABLE 5

Determination of presence of the fungal endophyte-derived insecticidal compound peramine in *Brachiaria-Urochloa* grass-fungal endophyte associations. Samples of *Brachiaria-Urochloa* grass-fungal endophyte associations were selected for metabolic profiling analysis. Three plants (biological replicates) from each group were analysed. Samples of the *Urocholoa mosambicensis* grass-fungal endophyte associations tested produced the endophyte-derived insecticidal compound peramine.

| Seed Batch | Species | Peramine (+/−) |
|---|---|---|
| 1 | *Brachiaria decumbens* | − |
| 2 | *Brachiaria humidicola*1 | − |
| 2 | *Brachiaria humidicola*2 | − |
| 3 | *Urocholoa mosambicensis* | + |
| 4 | *Brachiaria humidicola*1 | − |
| 4 | *Brachiaria humidicola*2 | − |
| 5 | *Brachiaria brizantha* | − |
| 6 | *Brachiaria decumbens* | − |
| 7 | *Brachiaria decumbens* | − |
| 8 | *Brachiaria humidicola*1 | − |
| 8 | *Brachiaria humidicola*2 | − |
| 9 | *Brachiaria humidicola* | − |
| 10 | *Brachiaria decumbens* | − |
| 11 | *Urocholoa mosambicensis* | + |
| 12 | *Urocholoa mosambicensis* | + |

TABLE 5-continued

Determination of presence of the fungal endophyte-derived insecticidal compound peramine in *Brachiaria-Urochloa* grass-fungal endophyte associations. Samples of *Brachiaria-Urochloa* grass-fungal endophyte associations were selected for metabolic profiling analysis. Three plants (biological replicates) from each group were analysed. Samples of the *Urocholoa mosambicensis* grass-fungal endophyte associations tested produced the endophyte-derived insecticidal compound peramine.

| Seed Batch | Species | Peramine (+/−) |
|---|---|---|
| 13 | *Brachiaria decumbens* | − |
| 14 | *Brachiaria decumbens* | − |
| 15 | *Brachiaria humidicola* | − |

EXAMPLE 6—ANTIFUNGAL ACTIVITY OF *ACREMONIUM* ENDOPHYTES ISOLATED FROM *BRACHIARIA/UROCHLOA* SPECIES COMPLEX

Figure 9:
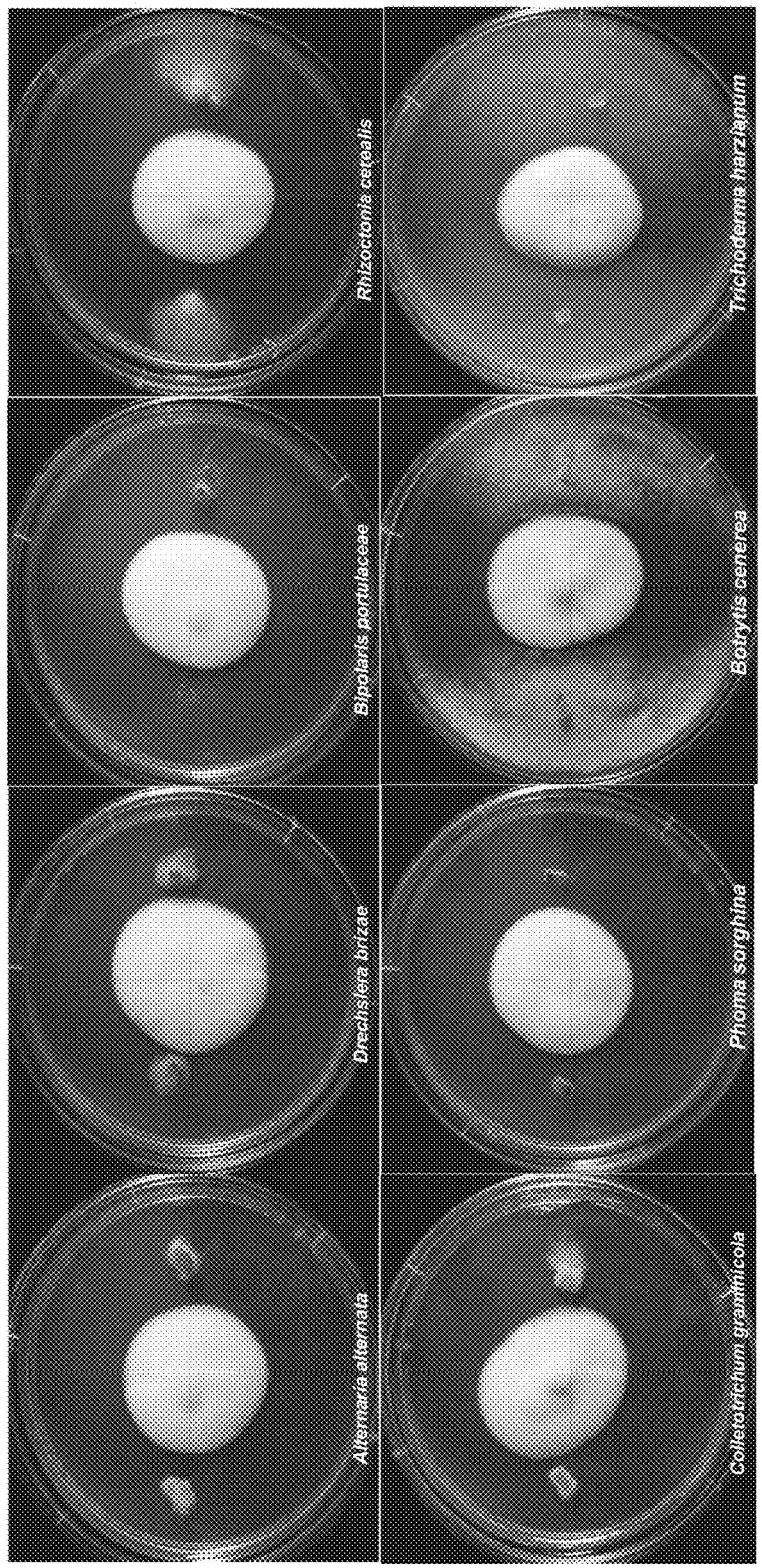
FIG. 9. An example of inhibition reactions in the antifungal assay. *Acremonium* endophyte isolate 9.2.A was tested for antifungal activity against 8 species of pathogenic fungi.

A previous publication reported antifungal activity in the *Acremonium implicatum* endophytic fungus isolated from *Brachiaria brizantha* (Kelemu et al. 2001). To investigate antifungal activity in the endophytes isolated here, all 29 *Acremonium* endophytic fungi were tested against 8 model test fungi: *Alternaria alternata, Colletotrichum graminicola, Rhizoctonia cerealis, Trichoderma harzianum, Phoma sorghina, Botrytis cinerea, Bipolaris portulaceae* and *Drechslera brizae*. Petri dishes containing potato dextrose agar were inoculated with a central colony of each endophyte isolate, and incubated 10 days at 24° C. Two inoculum of a model test fungus were then placed on opposite sides of each dish. Cultures were incubated at room temperature in the dark during 5 days and the size of the zone of inhibition was visually assessed on a scale of 0-5 (0—no inhibition; 1—very weak inhibition; 2—weak inhibition; 3—moderate inhibition; 4—strong inhibition; 5—very strong inhibition. For each endophyte-fungal pathogen combination five replicates were scored and the scores averaged. Endophyte isolate 9.2.A displayed strong, broad spectrum antifungal activity, inhibiting growth of all but *Botrytis cinerea* and *Trichoderma harzianum* (Table 6, FIG. 9). There were distinct differences in the level of antifungal activity across ITS groups—with group 3 (isolate 9.2.A) displaying the strongest, followed by group 2 (isolates 12.1.A and 12.1.D) and group 4 (5 isolates). Endophyte isolates within the ITS group 1 showed minimal inhibition of growth of pathogenic fungi (Table 6).

TABLE 6

Antifungal activity exhibited by endophytes from *Brachiaria* against plant pathogenic fungi. The size of the zone of inhibition was visually assessed on a scale of 0-5 (0 - no inhibition; 1 - very weak inhibition; 2 - weak inhibition; 3 - moderate inhibition; 4 - strong inhibition; 5 - very strong inhibition).

| Host Id | Endophyte Strain | Group (ITS) | *Bipolaris portulaceae* | *Colletotrichum graminicota* | *Rhizoctonia cerealis* | *Alternaria altemata* | *Drechsiera brizae* | *Phoma sorghina* | *Botrytis cinerea* | *Trichoderma harzianum* |
|---|---|---|---|---|---|---|---|---|---|---|
| B.b | 5.1.A | 1 | 1-2 | 1-2 | 1-2 | 0 | 1-2 | 3-4 | 1-2 | 0 |
| B.b | 5.1.B | 1 | 1-2 | 1-2 | 3-4 | 0 | 1-2 | 3-4 | 1-2 | 0 |
| B.b | 5.1.D | 1 | 3-4 | 1-2 | 1-2 | 0 | 3-4 | 3-4 | 1-2 | 0 |
| B.b | 5.1.E | 1 | 1-2 | 1-2 | 1-2 | 0 | 1-2 | 3-4 | 1-2 | 0 |
| B.d | 14.1.B | 1 | 1-2 | 1-2 | 3-4 | 1-2 | 3-4 | 3-4 | 3-4 | 0 |
| B.d | 14.1.C | 1 | 1-2 | 1-2 | 1-2 | 0 | 1-2 | 1-2 | 3-4 | 0 |
| B.d | 7.1.A | 1 | 1-2 | 1-2 | 1-2 | 0 | 1-2 | 1-2 | 3-4 | 0 |
| B.h1 | 15.2.C | 1 | 1-2 | 1-2 | 1-2 | 1-2 | 1-2 | 3-4 | 3-4 | 0 |
| B.h1 | 15.2.D | 1 | 1-2 | 1-2 | 1-2 | 0 | 1-2 | 1-2 | 3-4 | 0 |
| B.h1 | 15.2.E | 1 | 1-2 | 0 | 1-2 | 0 | 1-2 | 1-2 | 1-2 | 0 |
| B.h1 | 8.1.A | 1 | 1-2 | 1-2 | 1-2 | 0 | 1-2 | 1-2 | 1-2 | 0 |
| B.h1 | 8.1.B | 1 | 1-2 | 1-2 | 1-2 | 0 | 3-4 | 3-4 | 3-4 | 0 |
| B.h1 | 8.1.C | 1 | 1-2 | 1-2 | 1-2 | 0 | 3-4 | 3-4 | 3-4 | 0 |
| B.h1 | 9.2.C | 1 | 1-2 | 1-2 | 3-4 | 0 | 1-2 | 1-2 | 3-4 | 0 |
| B.h2 | 4.9.A | 1 | 1-2 | 1-2 | 1-2 | 0 | 1-2 | 3-4 | 1-2 | 0 |
| B.h2 | 4.9.B | 1 | 1-2 | 1-2 | 1-2 | 0 | 1-2 | 3-4 | 1-2 | 0 |
| U.m | 11.1.A | 1 | 3-4 | 1-2 | 3-4 | 0 | 3-4 | 1-2 | 3-4 | 0 |
| U.m | 12. 1.E | 1 | 1-2 | 1-2 | 3-4 | 0 | 1-2 | 1-2 | 3-4 | 0 |
| U.m | 3.3.A | 1 | 1-2 | 1-2 | 1-2 | 0 | 1-2 | 1-2 | 1-2 | 0 |
| U.m | 3.3.B | 1 | 1-2 | 1-2 | 1-2 | 0 | 1-2 | 1-2 | 3-4 | 0 |
| U.m | 3.3.C | 1 | 1-2 | 1-2 | 1-2 | 0 | 1-2 | 1-2 | 1-2 | 0 |
| B.d | 1.1.A | 2 | 1-2 | 3-4 | 5 | 1-2 | 1-2 | 1-2 | 1-2 | 1-2 |
| B.d | 10.1.A | 2 | 1-2 | 3-4 | 3-4 | 1-2 | 3-4 | 1-2 | 1-2 | 1-2 |
| B.h1 | 9.2.B | 2 | 1-2 | 5 | 3-4 | 0 | 1-2 | 3-4 | 1-2 | 1-2 |
| U.m | 12.1.B | 2 | 1-2 | 5 | 5 | 1-2 | 3-4 | 1-2 | 0 | 1-2 |
| U.m | 12.1.C | 2 | 1-2 | 3-4 | 5 | 3-4 | 3-4 | 1-2 | 0 | 1-2 |
| B.h1 | 9.2.A | 3 | 5 | 5 | 5 | 5 | 5 | 5 | 3-4 | 1-2 |
| U.m | 12.1.A | 4 | 3-4 | 5 | 5 | 1-2 | 3-4 | 1-2 | 3-4 | 1-2 |
| U.m | 12.1.D | 4 | 1-2 | 3-4 | 5 | 1-2 | 3-4 | 3-4 | 3-4 | 3-4 |

EXAMPLE 7—WHOLE GENOME SEQUENCING OF FUNGAL ENDOPHYTES ISOLATED FROM BRACHIARIA-UROCHLOA GRASSES

Methodologies for whole genome sequencing of fungal endophytes based on massive parallelisation of sequencing reactions have been established using sequencing platforms such as the Illumina HiSeq2000. High quality genomic DNA is prepared from mycelia samples from fungal endophytes isolated from *Brachiaria-Urochloa* grasses, sub-cultured in liquid media. DNA from each fungal endophyte strain is prepared for sequencing using established methodologies. Samples may be sequenced in multiplex using an indexing approach. The Illumina HiSeq2000 platform is based upon sequencing by synthesis approach, where millions of DNA fragments are bound to the surface of a glass flow cell and then amplified in situ to produce a discrete cluster of DNA strands. Sequencing is achieved by the addition of polymerase and 4 nucleotides differentially fluorescently labelled with an inactive 3'-OH group that ensures only a single nucleotide is incorporated with each cycle. Each base-incorporation is followed by image capture and then chemical cleavage to remove the fluorescent dye to enable base extension. The sequence is compiled by image overlay after sequence cycling is completed. Compiled sequences are checked for quality prior to genome assembly and analysis.

Five endophyte isolates (1.1.A, 3.3.A, 5.1.B, 9.2.A and 12.1.E) were sequenced using the Illumina HiSeq2000 platform. Paired end reads from each isolate were used as input for de novo genome sequence assembly. Analysis of assembled sequenced revealed isolates from within the same ITS group showed similar sequence assembly characteristics (Table 7).

Figure 11:
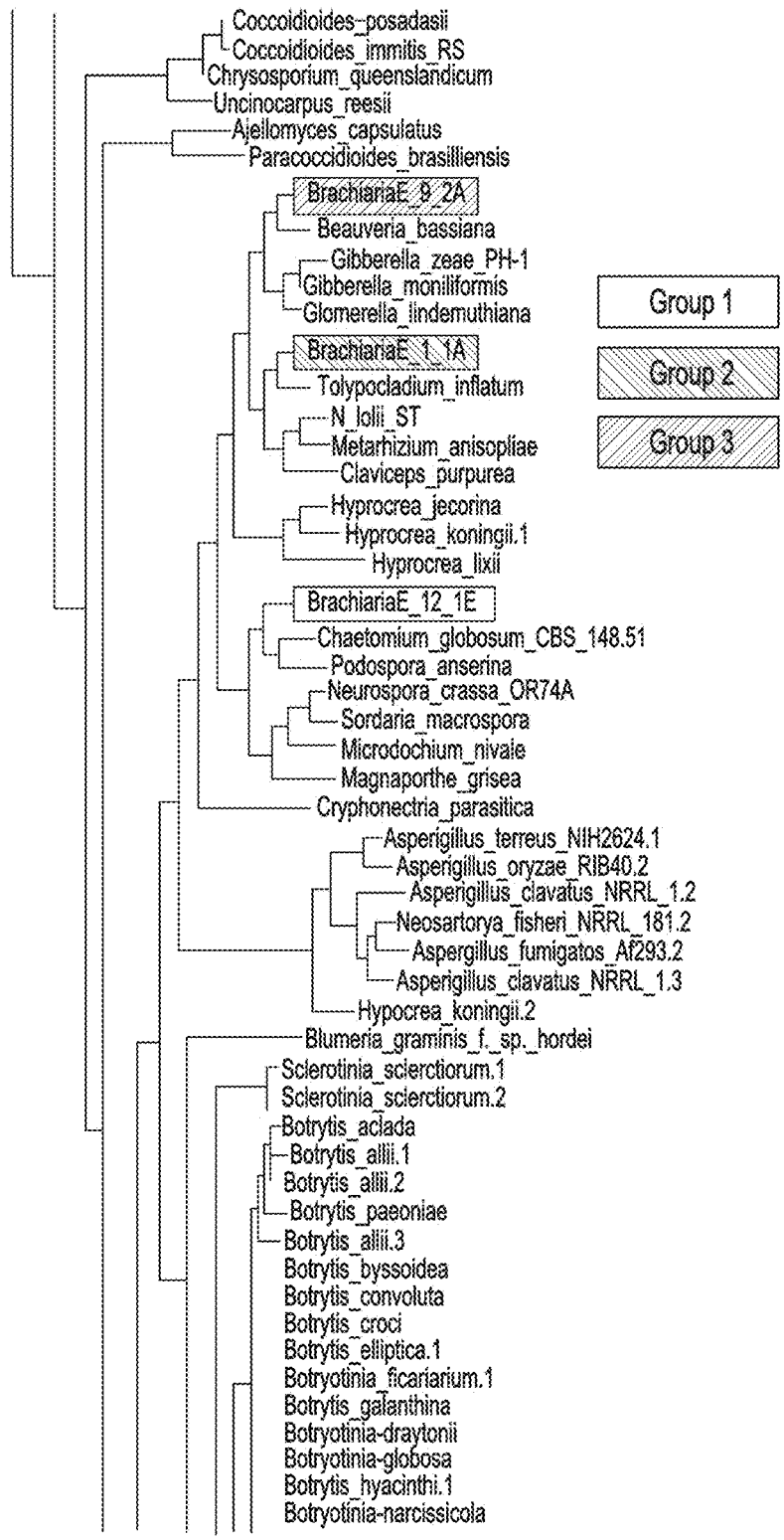
FIG. 11. Relevant section of a Neighbour-Joining tree derived from alignment of the GAPDH protein displaying the novel identity of 3 *Acremonium* isolates. *Acremonium* endophytes are highlighted to indicate ITS groups 1, 2 and 3. Note: only 1 *Acremonium* isolate (12.1.E) from ITS group 1 is displayed in the tree due to amino acid identity of GAPDH protein among members within this ITS group.

To investigate the level of diversity among the 5 endophyte strains (1.1.A, 3.3.A, 5.1.B, 9.2.A and 12.1.E), the GAPDH gene was identified by using the *Neurospora crassa* GAPDH cDNA sequence as a query in a BLASTn search of a sequence database comprising contigs from the 5 endophyte isolates. The GAPDH gene sequences were polymorphic between ITS groups, but highly similar within groups (FIG. 10), suggesting isolates 3.3.A, 5.1.B and 12.1.E may be the same strain. Phylogenetic analysis of the GAPDH protein confirmed the 3 ITS groups to which isolates 1.1.A, 9.2.A and 12.1.E belong to are divergent from one another and all other fungi within an in-house fungal database (FIG. 11).

To further interrogate the level of diversity among the 3 isolates belonging to ITS group 1, the *Epichloe festucae* peramine A gene (perA) (GenBank Accession #BAE06845) and homologous genes within ITS group 1 endophytes 3.3.A, 5.1.B and 12.1.E were aligned. Sequence polymorphism was observed within ITS group 1 isolates possibly suggesting different strains (FIG. 12).

It will be understood that the invention disclosed and defined in this specification extends to all alternative combinations of two or more of the individual features mentioned or evident from the text or drawings. All of these different combinations constitute various alternative aspects of the invention.

REFERENCES

Jungmann, L., A. C. B. Sousa, et al. (2009). Isolation and characterization of microsatellite markers for *Brachiaria brizantha* (Hochst. ex A. Rich.) Stap. Conservation Genetics 10(6): 1873-1876.

Kelemu, S., White J. F., Jr., et al. (2001). "An endophyte of the tropical forage grass *Brachiaria brizantha*: Isolating, identifying, and characterizing the fungus, and determining its antimycotic properties." Canadian Journal of Microbiology 47(1): 55-62.

White, T. J., Bruns, T., Lee, S., and Taylor, J. (1990) Amplification and direct sequencing of fungal ribosomal RNA genes for phylogenetics. In PCR Protocols: A Guide to Methods and Applications pp. 315-322. Academic Press.

TABLE 7

| ITS-Group | Isolate | Assembled Size | # Contigs >100 bp | Largest Contig | N50 | # reads input | # reads used |
|---|---|---|---|---|---|---|---|
| 1 | 3.3.A | 33,194,262 | 6,173 | 282,024 | 23,771 | 23,286,068 | 19,779,082 |
| 1 | 5.1.B | 33,453,571 | 5,937 | 331,319 | 34,056 | 35,030,948 | 29,733,043 |
| 1 | 12.1.E | 33,707,236 | 6,168 | 250,614 | 25,466 | 17,237,708 | 15,676,548 |
| 2 | 1.1.A | 33,542,777 | 2,529 | 1,912,494 | 302,046 | 19,152,972 | 17,145,454 |
| 4 | 9.2.A | 29,635,075 | 1,705 | 1,830,966 | 584,893 | 25,280,459 | 26,552,756 |

The claims defining the invention are as follows:

1. A method of increasing resistance to pests and/or diseases in a plant, said method comprising the step of inoculating said plant with a fungi of *Acremonium* spp., wherein, when said fungus is inoculated into the plant, said plant has improved resistance to diseases and/or pests relative to an uninoculated control plant and wherein the internal transcribed spacer (ITS) of said fungi has 99% or greater sequence identity with the internal transcribed spacer of *Acremonium* 9.2A or *Acremonium* 3.3A.

2. The method according to claim 1, wherein said increased resistance to pests and/or diseases is selected from the group consisting of insecticidal activity, insect repellent activity and antifungal activity.

3. The method according to claim 1, wherein said fungus is purified or isolated from a plant of the *Brachiaria-Urochloa* species complex.

4. The method according to claim 3, wherein said plant of the *Brachiaria-Urochloa* complex is selected from the group consisting of *Brachiaria brizantha, Brachiaria decumbens, Brachiaria humidicola* and *Urochloa mosambicensis*.

5. The method according to claim 3, wherein said fungus is isolated by a method including providing a plurality of samples of fungi;
    subjecting said fungi to genetic analysis;
    subjecting said fungi to metabolic analysis; and
    selecting fungi having a desired genetic and metabolic profile.

6. The method according to claim 5, wherein said method further includes the step of assessing geographic origin of the fungi and selecting fungi having a desired genetic and metabolic profile and a desired geographic origin.

7. The method according to claim 5, wherein said genetic analysis includes detecting the presence or absence of polymorphic markers.

8. The method according to claim 3, wherein said plant of the *Brachiaria-Urochloa* complex is selected from the group consisting of *Brachiaria brizantha, Brachiaria decumbens, Brachiaria humidicola, Brachiaria stolonifera, Brachiaria ruziziensis, Urochloa brizantha, Urochloa decumbens, Urochloa humidicola, Urochloa mosambicensis, Brachiaria marlothii, Brachiaria nigropedata, Urochloa dictyoneura, Urochloa oligotricha, Urochloa panicoides, Brachiaria obtusiflora, Brachiaria serrifolia, Urochloa advena, Urochloa arrecta, Urochloa brachyura, Urochloa eminii, Urochloa mollis, Urochloa xantholeuca, Urochloa oligotricha, Urochloa panicoides, Urochloa plantaginea, Urochloa platynota* and *Urochloa xantholeuca*.

9. The method according to claim 1, wherein said fungus is selected from the group consisting of *Acremonium* 9.2A, *Acremonium* 3.3A and *Acremonium* 5.1B.

10. The method of claim 1, wherein the inoculated plant is a grass species.

11. The method of claim 10, wherein the inoculated plant is a forage, turf or bioenergy grass.

12. The method of claim 11, wherein the inoculated plant is a member of the *Brachiaria-Urochloa* species complex.

13. The method of claim 11, wherein the inoculated plant is a member of the genera *Lolium* or *Festuca*.

14. A method of increasing resistance to pests and/or diseases in a plant, said method comprising the step of inoculating said plant with a fungi of *Acremonium* spp., wherein, when said fungus is inoculated into the plant, said plant has improved resistance to diseases and/or pests relative to an uninoculated control plant and wherein the internal transcribed spacer (ITS) of said fungi has 99% or greater sequence identity with the internal transcribed spacer of *Acremonium* 3.3A.

* * * * *